(12) United States Patent
Malone

(10) Patent No.: US 7,837,735 B2
(45) Date of Patent: Nov. 23, 2010

(54) DEVICES AND METHODS FOR FACILITATING CONTROLLED BONE GROWTH OR REPAIR

(75) Inventor: David G. Malone, Tulsa, OK (US)

(73) Assignee: DePuy Spine, Inc., Raynham, MA (US)

( * ) Notice: Subject to any disclaimer, the term of this patent is extended or adjusted under 35 U.S.C. 154(b) by 949 days.

(21) Appl. No.: 10/812,837

(22) Filed: Mar. 30, 2004

(65) Prior Publication Data
US 2004/0225360 A1 Nov. 11, 2004

Related U.S. Application Data

(63) Continuation-in-part of application No. PCT/US02/23262, filed on Jul. 23, 2002, which is a continuation-in-part of application No. 09/737,074, filed on Dec. 14, 2000, now abandoned.

(51) Int. Cl.
*A61F 2/44* (2006.01)

(52) U.S. Cl. .................................................. 623/17.16

(58) Field of Classification Search ... 623/17.11–17.16, 623/16.11, 18.11
See application file for complete search history.

(56) References Cited

U.S. PATENT DOCUMENTS

| | | | |
|---|---|---|---|
| 4,501,269 A | 2/1985 | Bagby | |
| 4,820,305 A | 4/1989 | Harms et al. | |
| 4,961,740 A | 10/1990 | Ray et al. | |
| 5,015,247 A | 5/1991 | Michelson | |
| 5,026,373 A * | 6/1991 | Ray et al. | ...................... 606/61 |
| 5,055,104 A | 10/1991 | Ray | |
| 5,123,705 A | 6/1992 | Johnson | |

(Continued)

FOREIGN PATENT DOCUMENTS

EP 369603 A1 5/1990

(Continued)

OTHER PUBLICATIONS

Agazzi, S., et al., "Posterior lumbar interbody fusion with cages: an independent review of 71 cases," J Neurosurg (Spine 2), vol. 91, pp. 186-192, (1999).

(Continued)

*Primary Examiner*—Alvin J. Stewart
(74) *Attorney, Agent, or Firm*—Nutter McClennen & Fish LLP

(57) ABSTRACT

Bone implantable devices and methodologies permit careful application of biologically active substances and management of bone growth processes. The device includes a body defining a carrier receiving area for locating adjacent bone. Carrier material is located in the carrier receiving area. Substance is delivered onto carrier material through a port. A pathway delivers substance from the carrier receiving area to the bone surface. The body may be in the form of a spinal fusion cage, facet fusion screw, artificial joint, bone fixation plate, interbody graft, IM nail, hip stem, or other bone-to-bone appliances or bone-to-device appliances. In use, carrier is installed in the carrier receiving area of the device. The device is then implanted adjacent a bone. The substance is applied to the carrier for subsequent delivery to the bone. By doping carrier material after device implantation, inadvertent contact of the substance with non-target bone is more easily eliminated.

7 Claims, 12 Drawing Sheets

U.S. PATENT DOCUMENTS

| | | | |
|---|---|---|---|
| 5,489,308 A | 2/1996 | Kuslich et al. | |
| 5,534,031 A | 7/1996 | Matsuzaki et al. | |
| 5,571,189 A * | 11/1996 | Kuslich | 623/17.12 |
| 5,571,192 A | 11/1996 | Schonhoffer | |
| D377,095 S | 12/1996 | Michelson | |
| 5,593,409 A | 1/1997 | Michelson | |
| 5,609,636 A | 3/1997 | Kohrs et al. | |
| 5,669,909 A | 9/1997 | Zdeblick et al. | |
| 5,683,394 A | 11/1997 | Rinner | |
| 5,683,459 A * | 11/1997 | Brekke | 424/423 |
| 5,683,463 A | 11/1997 | Godefroy et al. | |
| 5,693,100 A * | 12/1997 | Pisharodi | 623/17.16 |
| 5,702,449 A | 12/1997 | McKay | |
| 5,709,683 A | 1/1998 | Bagby | |
| 5,755,798 A | 5/1998 | Papavero et al. | 623/17 |
| 5,766,253 A | 6/1998 | Brosnahan, III | |
| 5,776,196 A | 7/1998 | Matsuzaki et al. | |
| 5,776,197 A * | 7/1998 | Rabbe et al. | 623/17.15 |
| 5,782,919 A | 7/1998 | Zdeblick et al. | |
| 5,785,710 A | 7/1998 | Michelson | |
| 5,800,550 A * | 9/1998 | Sertich | 623/17.16 |
| 5,846,484 A | 12/1998 | Scarborough et al. | |
| 5,860,973 A | 1/1999 | Michelson | |
| 5,876,457 A | 3/1999 | Picha et al. | |
| 5,885,287 A | 3/1999 | Bagby | |
| 5,888,222 A | 3/1999 | Coates et al. | 623/17 |
| 5,888,228 A * | 3/1999 | Knothe et al. | 623/17.16 |
| 5,906,616 A | 5/1999 | Pavlov et al. | |
| 5,928,284 A * | 7/1999 | Mehdizadeh | 623/17.13 |
| 5,968,099 A | 10/1999 | Badorf et al. | |
| 5,976,187 A | 11/1999 | Richelsoph | |
| 5,980,522 A | 11/1999 | Koros et al. | |
| 5,984,967 A | 11/1999 | Zdeblick et al. | |
| 6,010,502 A | 1/2000 | Bagby | |
| 6,015,436 A * | 1/2000 | Schonhoffer | 623/17.16 |
| 6,022,376 A | 2/2000 | Assell et al. | 623/17 |
| 6,039,762 A | 3/2000 | McKay | |
| 6,066,175 A | 5/2000 | Henderson et al. | |
| 6,071,310 A | 6/2000 | Picha et al. | |
| 6,074,423 A | 6/2000 | Lawson | |
| 6,093,207 A | 7/2000 | Pisharodi | |
| 6,099,531 A | 8/2000 | Bonutti | |
| 6,102,948 A | 8/2000 | Brosnahan, III | |
| 6,120,506 A | 9/2000 | Kohrs et al. | |
| 6,126,688 A * | 10/2000 | McDonnell | 623/17.16 |
| 6,149,650 A | 11/2000 | Michelson | |
| 6,149,686 A | 11/2000 | Kuslich et al. | |
| 6,165,219 A | 12/2000 | Kohrs et al. | |
| 6,168,631 B1 | 1/2001 | Maxwell et al. | |
| 6,179,873 B1 | 1/2001 | Zientek | |
| 6,200,348 B1 * | 3/2001 | Biedermann et al. | 623/17.11 |
| 6,241,770 B1 | 6/2001 | Michelson | |
| 6,264,656 B1 | 7/2001 | Michelson | |
| 6,283,998 B1 * | 9/2001 | Eaton | 623/17.16 |
| 6,287,343 B1 | 9/2001 | Kuslich et al. | |
| 6,346,122 B1 | 2/2002 | Picha et al. | |
| 6,368,322 B1 | 4/2002 | Luks et al. | |
| 6,375,655 B1 | 4/2002 | Zdeblick et al. | |
| 6,375,681 B1 * | 4/2002 | Truscott | 623/17.11 |
| 6,391,058 B1 | 5/2002 | Kuslich et al. | |
| 6,409,764 B1 * | 6/2002 | White et al. | 623/16.11 |
| 6,409,766 B1 | 6/2002 | Brett | |
| 6,419,704 B1 * | 7/2002 | Ferree | 623/17.12 |
| D461,248 S | 8/2002 | Bianchi et al. | |
| 6,428,575 B2 | 8/2002 | Koo et al. | |
| 6,436,141 B2 | 8/2002 | Castro et al. | |
| 6,454,807 B1 | 9/2002 | Jackson | |
| 6,471,724 B2 | 10/2002 | Zdeblick et al. | |
| 6,482,234 B1 * | 11/2002 | Weber et al. | 623/17.12 |
| 6,527,805 B2 | 3/2003 | Studer et al. | |
| 6,558,423 B1 | 5/2003 | Michelson | |
| 6,605,089 B1 * | 8/2003 | Michelson | 606/32 |
| 6,613,084 B2 | 9/2003 | Yang | 623/1.42 |
| 6,613,091 B1 | 9/2003 | Zdeblick et al. | |
| 6,645,206 B1 | 11/2003 | Zdeblick et al. | |
| 6,726,722 B2 | 4/2004 | Walkenhorst et al. | |
| 6,758,849 B1 | 7/2004 | Michelson | |
| 6,758,862 B2 * | 7/2004 | Berry et al. | 623/17.16 |
| 6,776,798 B2 * | 8/2004 | Camino et al. | 623/17.16 |
| 6,783,545 B2 | 8/2004 | Castro et al. | |
| 6,808,538 B2 * | 10/2004 | Paponneau | 623/17.16 |
| 6,821,298 B1 * | 11/2004 | Jackson | 623/17.15 |
| 6,835,206 B2 * | 12/2004 | Jackson | 623/17.11 |
| 6,890,355 B2 | 5/2005 | Michelson | |
| 6,902,578 B1 | 6/2005 | Anderson et al. | |
| 7,182,781 B1 | 2/2007 | Bianchi et al. | |
| 7,288,093 B2 | 10/2007 | Michelson | |
| 7,537,616 B1 * | 5/2009 | Branch et al. | 623/17.16 |
| 2001/0010020 A1 | 7/2001 | Michelson | |
| 2001/0032018 A1 | 10/2001 | Castro et al. | |
| 2002/0035400 A1 * | 3/2002 | Bryan et al. | 623/17.15 |
| 2002/0040242 A1 | 4/2002 | Picha et al. | |
| 2002/0040243 A1 * | 4/2002 | Attali et al. | 623/17.16 |
| 2002/0055782 A1 | 5/2002 | Bagby | |
| 2002/0116064 A1 | 8/2002 | Middleton | |
| 2002/0116065 A1 * | 8/2002 | Jackson | 623/17.16 |
| 2002/0138144 A1 | 9/2002 | Michelson | |
| 2002/0138147 A1 | 9/2002 | Cohen | |
| 2002/0169507 A1 | 11/2002 | Malone | |
| 2002/0183846 A1 * | 12/2002 | Kuslich et al. | 623/17.11 |
| 2002/0183847 A1 * | 12/2002 | Lieberman | 623/17.11 |
| 2003/0009222 A1 | 1/2003 | Fruh et al. | |
| 2003/0105527 A1 | 6/2003 | Bresina | |
| 2003/0114854 A1 | 6/2003 | Pavlov et al. | |
| 2003/0114930 A1 | 6/2003 | Lim et al. | |
| 2003/0139816 A1 | 7/2003 | Michelson | |
| 2004/0064185 A1 | 4/2004 | Michelson | |
| 2004/0097928 A1 | 5/2004 | Zdeblick et al. | |
| 2004/0111093 A1 | 6/2004 | Chappuis | |
| 2004/0133277 A1 | 7/2004 | Michelson | |
| 2004/0172019 A1 | 9/2004 | Ferree | |
| 2005/0015150 A1 * | 1/2005 | Lee | 623/17.12 |
| 2005/0038513 A1 | 2/2005 | Michelson | |
| 2005/0049705 A1 | 3/2005 | Hale et al. | |
| 2005/0080486 A1 | 4/2005 | Fallin et al. | |
| 2005/0090901 A1 * | 4/2005 | Studer | 623/17.12 |
| 2006/0064099 A1 | 3/2006 | Pavlov et al. | |
| 2006/0085068 A1 | 4/2006 | Barry | |
| 2006/0111779 A1 | 5/2006 | Petersen | |
| 2006/0111782 A1 | 5/2006 | Petersen | |
| 2007/0083265 A1 | 4/2007 | Malone | |
| 2007/0173519 A1 | 7/2007 | Lavi | |
| 2008/0154374 A1 | 6/2008 | Labrom | |

FOREIGN PATENT DOCUMENTS

| | | |
|---|---|---|
| EP | 0716840 A2 | 7/1996 |
| EP | 1114625 A1 | 7/2001 |
| EP | 1400221 A2 | 3/2004 |
| FR | 2760355 A | 7/1998 |
| WO | 9106261 A1 | 5/1991 |
| WO | 9627339 A1 | 9/1996 |
| WO | 9640020 A1 | 12/1996 |
| WO | PCT/US02/23262 | 7/2002 |
| WO | 2004008999 A1 | 1/2004 |

OTHER PUBLICATIONS

Goh, J.C.H., et al., "Influence of PLIF Cage Size on Lumbar Spine Stability," Spine, vol. 25 (No. 1), pp. 35-40, (2000), Lippincott Williams & Wilkins, Inc.

Greenough, C.G., et al., "Anteriror Lumbar Fusion. A Comparison of Noncompensation Patients with Compensation Patients," Clinical Orthopaedics and Related Research, No. 300, pp. 30-37, (1994), J.B. Lippincott Company.

Hacker, R.J., "Comparison of Interbody Fusion Approaches for Disabling Low Back Pain," Spine, vol. 22 (No. 6), pp. 660-666, (1997), Lippincott-Raven Publishers.

Highhouse, M.E., et al., "Lateral Intertransverse Process Single-Level Fusion for Salvage of the Unstable Failed Posterior Lumbar Interbody Fusion," Journal of Spinal Disorders, vol. 9 (No. 1), pp. 59-63, (1996), Lippincott-Raven Publishers.

Kuslich, S.D., et al., "The Bagby and Kuslich Method of Lumbar Interbody Fusion. History, Techniques, and 2-Year Follow-up Results of a United States Prospective, Multicenter Trial," Spine, vol. 23 (No. 11), pp. 1267-1279, (1998), Lippincott-Raven Publishers.

McAfee, P.C., et al., "Miminally Invasive Anterior Retroperitoneal Approach to the Lumbar Spine. Emphasis on the Lateral Bak," Spine, vol. 23 (No. 13), pp. 1476-1484, (1998), Lippincott-Raven Publishers.

McAfee, P.C., et al., "Revision Strategies for Salvaging or Improving Failed Cylindrical Cages," Spine, vol. 24 (No. 20), pp. 2147-2153, (1999), Lippincott Williams & Wilkins, Inc.

Schlegel, K. F., et al., "The Biomechanics of Posterior Lumbar Interbody Fusion (PLIF) in Spondylolisthesis," Clinical Orthopaedics and Related Research, No. 193, pp. 115-119, (1985).

Vamvanij, V., et al., "Surgical Treatment of Internal Disc Disruption: An Outcome Study of Four Fusion Techniques," Journal of Spinal Disorders, vol. 11 (No. 5), pp. 375-382, (1998), Lippincott Williams & Wilkins (Philadelphia).

Voor, M.J., et al., "Biomechanical Evaluation of Posterior and Anterior Lumbar Interbody Fusion Techniques," Journal of Spinal Disorders, vol. 11 (No. 4), pp. 328-334, (1998), Lippincott Williams & Wilkins (Philadelphia).

Zhao, J., et al., "Posterior Lumbar Interbody Fusion Using Posterolateral Placement of a Single Cylindrical Threaded Cage," Spine, vol. 25 (No. 4), pp. 425-430, (2000), Lippincott Williams & Wilkins, Inc.

U.S. Appl. No. 09/737,074, Malone.

Bagby, Arthrodesis by the Distraction-Compression Method Using a Stainless Steel Implant, Orthopaedics 1998, vol. 11:931-4.

Brantigan, "A CarbonFibre Implant to Aid Interbody Lumbar Fusion", Spine 1991, 16(Suppl):S277-82 (with Steffee and Geiger).

Ray. "Threaded Titanium Cages for Lumbar Interbody Fusions", Spine 1997, 22:667-80.

Kandziora, Biomechanical Testing of the Lumbar Facet Interference Screw, Spine, 2005; vol. 32, No. 2, pp. E34-E39.

* cited by examiner

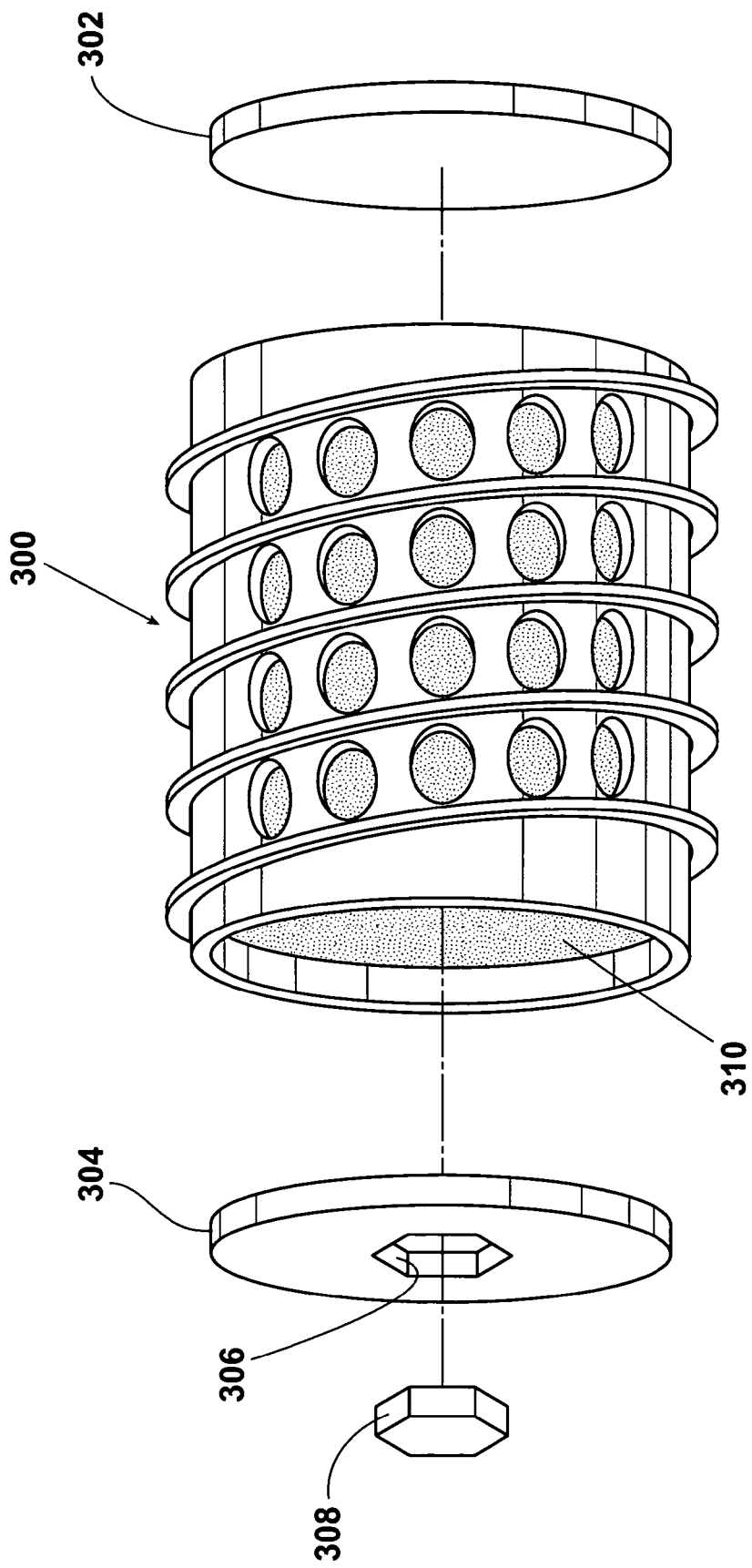

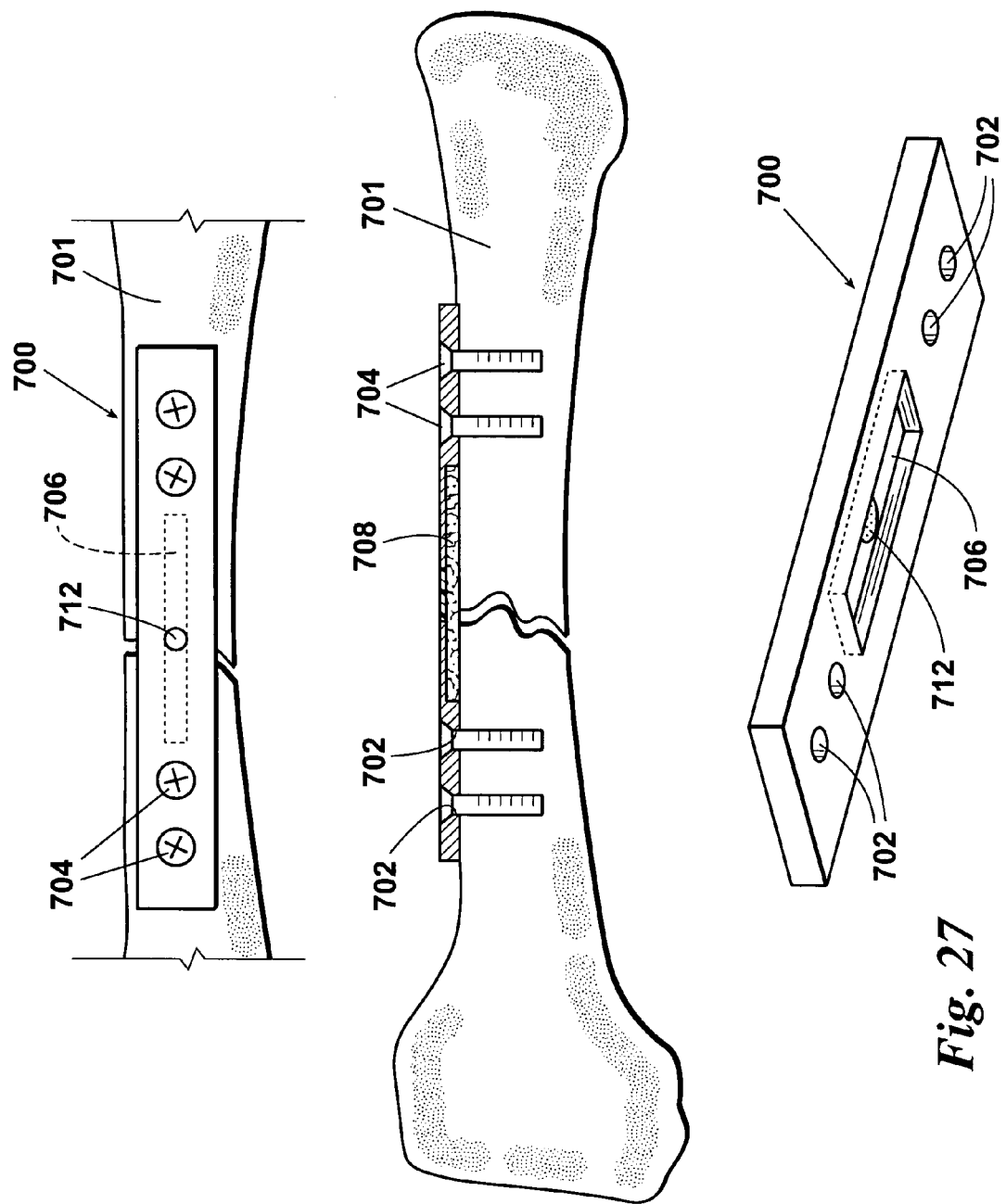

DEVICES AND METHODS FOR FACILITATING CONTROLLED BONE GROWTH OR REPAIR

CROSS REFERENCE TO RELATED APPLICATIONS

This application is a continuation-in-part of co-pending International Application No. PCT/US02/23262, filed Jul. 23, 2002, which International Application designates the United States and which itself is a continuation-in-part of U.S. patent application Ser. No. 09/737,074, filed Dec. 14, 2000, now abandoned, to which priority is claimed.

BACKGROUND OF THE INVENTION

1. Technical Field

This invention is directed generally to devices and methods for facilitating bone growth, and, in particular, to bone implantable devices and implantation methodologies that augment beneficial bone growth or repair while limiting bone growth in undesirable directions.

2. Background

In orthopedic and neurological surgical procedures it is often important to facilitate the growth or fusion of bony structures. This may entail growth "bone-to-bone" or, depending on the nature of the procedure, bone to device.

Chronic back problems, for example, cause pain and disability for a large segment of the population. In many cases, such problems are attributable to relative movement between vertebrae in the spine. Spinal surgery includes procedures to stabilize adjacent vertebrae. Common stabilization methods often involve fusing adjacent vertebrae together.

Fusion techniques include removing disc material that separates the vertebrae and impacting bone into the disc area. The impacted bone fuses with the bone material of the two adjacent vertebrae to thereby fuse the vertebrae together.

In a further advance in the art, spinal implants have been developed to increase the probability of a successful fusion. Such devices generally comprise a hollow cage into which bone growth inducing substances, such as bone chips or bone slurry, may be placed. The cage is inserted, either by anterior or posterior approach, into the intervertebral disc space. The cage wall has holes extending radially therethrough, typically throughout the entire cage surface. Bone growth extends into the device through the radial apertures, facilitating arthrodesis between the adjacent vertebral bone structures and allowing for the decompression of neural elements.

With the continued development of techniques for achieving spinal fusion through the use of spine fusion cages, new materials have been developed to augment the fusion process. Traditionally, the patient's own bone, or cadaver bone, was used in the cage to promote bony fusion. More recently, powerful new biologic materials have been discovered that greatly accelerate the fusion process, in some cases eliminating the need for donor bone.

However, with the utilization of the newer biologic materials there has arisen a significant problem. When bone growth inducing agents, such as bone morphogenic proteins ("BMP"), are used in cages of existing design there is risk of inducing the overgrowth of bone around and into sensitive neural tissues. This is especially the case when a posterior approach is utilized to implant a spinal fusion cage, as bony overgrowth toward the central canal or neural foramen may impinge on spinal nerve roots causing neurological damage. A recent study on posterior lumbar interbody fusion procedures using rhBMP-2 reported that 58% of patients experienced greater than expected bone formation dorsal to the fusion cage. In 30% of the cases, the bony overgrowth compromised the central canal, the neural foramen, or both. This study is confirmatory to observations first made by the present inventor in early 1999.

Typically, the bone growth agent is in liquid form and is applied to an absorbent carrier material, such as a piece of bovine collagen. The doped carrier material is placed with forceps into the interbody space, usually into an open end of the fusion cage after the cage has been implanted, but sometimes prior to cage implantation. During placement carrier material may inadvertently wipe across body areas, including internal bony structures, where bone growth is not desired. In addition, as the carrier material is pressed into place agent may squeeze out and flow into adjacent areas. Exacerbating the problem, current protocols do not encourage the use of suction, irrigation and hemostatic agents when bone growth agent is utilized. Conventional cage design also allows for the leakage of agent into undesirable areas after implantation through ill-placed apertures in the cage body, in the cage end caps, or otherwise. Because of the powerful stimulatory effects of bone growth agents, uncontrolled application of these substances may lead to serious complications, including severe inflammation, debilitating neural impingement, and other potential complications.

Thus, there is a need to better control the bone growth process when using a bone implantable device, especially in circumstances where powerful bone growth inducing agents are used in conjunction therewith.

In satisfying this need, there is also an opportunity to extend the application of bone growth agent based bony fusion to all types of bone implantable devices to better achieve union of bone-to-bone or bone-to-device, as the case may be.

SUMMARY OF THE INVENTION

In connection with the present invention, there are provided bone implantable devices and implantation methodologies that allow for the careful application of bone growth inducing agents, e.g. BMP, and management of bone growth processes.

In accordance with one aspect of the present invention, there is provided a bone implantable device and carrier combination, which combination is implanted into the body prior to application of bone growth agent to the carrier. After the device is implanted, the bone growth agent may be applied to the carrier in a manner avoiding its contact with non-target body structures.

In one embodiment the bone implantable device includes a conveniently placed injection port that communicates with the carrier material. After implantation of the device bone growth agent is applied to the carrier material through the injection port.

In another embodiment, the bone implantable device includes a hollow interior structure in which carrier material is located. After implantation of the device the bone growth agent is injected into the carrier material through an injection port. One or more apertures communicating with the hollow interior are located on the portion of the device that is, upon implantation, adjacent target bone structure, allowing for the controlled delivery of bone growth agent to the target bone structure.

In still another embodiment, a plenum is provided in the hollow interior of a bone implantable device to facilitate the even distribution of bone growth agent from the injection port into the carrier material.

The bone implantable device may take the form of an interbody spinal fusion cage, a facet fusion screw, an artificial joint, a bone fixation plate, an intervertebral body graft, an IM nail, a hip stem, and other orthopedic appliances where promoting bone-to-bone growth or growth from bone into the device is beneficial. The bone implantable device itself is so constructed as to allow the bone growth agent to flow therefrom only in desired directions, i.e. to target bone structures. Many non-limiting examples are provided herein for illustrative purposes.

As primary examples of device construction for vertebral fusion purposes, there are provided several embodiments of a fusion cage which can be inserted into an intervertebral disc space using either a posterior or anterior approach and which prevents overgrowth of bone around or into neural tissue. Growth of bone into sensitive areas is prohibited by providing the cage with various zones wherein the cage wall is either perforated or non-perforated. A cage body is provided having a posterior end and an anterior end and defining an internal cavity and a longitudinal axis. The cage body has an outer surface and a plurality of apertures extending from the outer surface and communicating with the internal cavity in a preselected pattern. Preferably, there is a first non-perforated zone extending from the posterior end of the cage a preselected length toward its anterior end, second and third non-perforated zones on the longitudinal sides, wherein non-perforated zones are defined by the medial sides of the cage extending in opposing relation from the first zone further toward the anterior end, and two opposed perforated zones oriented so that upon insertion of the device the perforated zones will be adjacent the vertebral bodies to be fused, which channels the bone growth in a superior and inferior direction only to allow bone growth across the vertebral interspace. Each end of the cage is provided with a non-perforated closure. Preferably, the posterior end is closed completely, while the anterior end may or may not be closed. In this manner bone growth is prevented in areas adjacent the non-perforated zones when the fusion cage is in place.

In another example there is provided a novel spine fusion cage which provides for the selective occlusion of apertures in the cage wall so as to prevent the growth of bone in undesired directions. As an example, there is provided an inventive cage having outer and inner cage elements. An outer cage body having a posterior end and an anterior end defines an internal cavity. A plurality of apertures extends through the outer surface of the outer cage body to communicate with the internal cavity in a pattern covering a substantial portion of the outer surface of the cage body. An inner cage body is disposed within the internal cavity of the outer cage body and is positioned as to form an annulus between the inner wall surface of the outer cage body and the outer wall surface of the inner cage body. The inner cage body likewise has a plurality of apertures extending through its outer surface so as to establish communication with the annulus and the outer surface of the outer cage. An end closure means having occluding surfaces suitable for introduction into the annulus between the outer and inner cages serves to establish one or more desired zones or patterns of occluded apertures amongst the plurality of apertures in the outer cage body, thereby obstructing bone growth in undesired directions.

In still another example there is provided an end closure means for effecting the closure of the posterior end of a fusion cage while establishing a desired occlusion pattern of apertures in the wall of the fusion cage. The closure means comprises a non-perforated sealing member to effect the closure of the posterior end of the internal cavity of the fusion cage and one or more occluding surfaces extending from the sealing member essentially parallel to the longitudinal axis of the fusion cage so as to establish one or more desired zones or patterns of occluded apertures amongst the plurality of apertures in the cage body.

In still another example, a cage body is provided that has a posterior end and an anterior end and defines an internal cavity. The cage body further has an outer surface and a plurality of apertures extending through the outer surface in communication with the internal cavity, wherein the outer surface has a preselected pattern of perforated and non-perforated zones. A first end closure is secured at a first end of said cage body. A second end closure is provided that has an orifice therein. The second end closure is secured at a second end of the cage body. At least one of the first end closure and the second end closure is removable so as to provide access to the internal cavity. A plug is located in the orifice that is capable of being penetrated by a syringe needle for administering a bone growth agent to said internal cavity. Preferably, a carrier that is compatible with a bone growth or biologic agent and that holds and dispenses the agent in a time released and controlled fashion, receives the bone growth agent. By using this approach, chances for misapplication of bone growth material are greatly diminished. A plenum is preferably used to encourage even application of the bone growth agent to the carrier material.

Further examples as related to other orthopedic appliances are also provided.

In addition, in accordance with another aspect of the present invention there is provided a methodology for implanting bone implantable devices wherein the device and carrier material are implanted into the body in their operative positions prior to the loading of bone growth agent into the carrier material.

In one embodiment, the carrier material is isolated within the bone implantable device prior to application of the bone growth agent to the carrier material.

In a preferred embodiment, the bone growth agent is applied to the carrier material via an injection port.

In another preferred embodiment, bone growth agent is applied to the carrier material through a plenum communicating with an injection port.

A better understanding of the present invention, its several aspects, and its advantages will become apparent to those skilled in the art from the following detailed description, taken in conjunction with the attached drawings, wherein there is shown and described the preferred embodiments of the invention, simply by way of illustration of the best mode contemplated for carrying out the invention.

BRIEF DESCRIPTION OF THE DRAWINGS

FIG. 13 is an exploded perspective view of an embodiment of an inventive cage having an end cap and an injection port.

FIG. 25 is a side view of a bone implantable structure located on a bone structure.

FIG. 26 is a top view of the bone implantable structure of FIG. 25.

FIG. 27 is an enlarged perspective view of the bone implantable structure of FIG. 27.

DETAILED DESCRIPTION OF THE PREFERRED EMBODIMENTS

Figure 1:
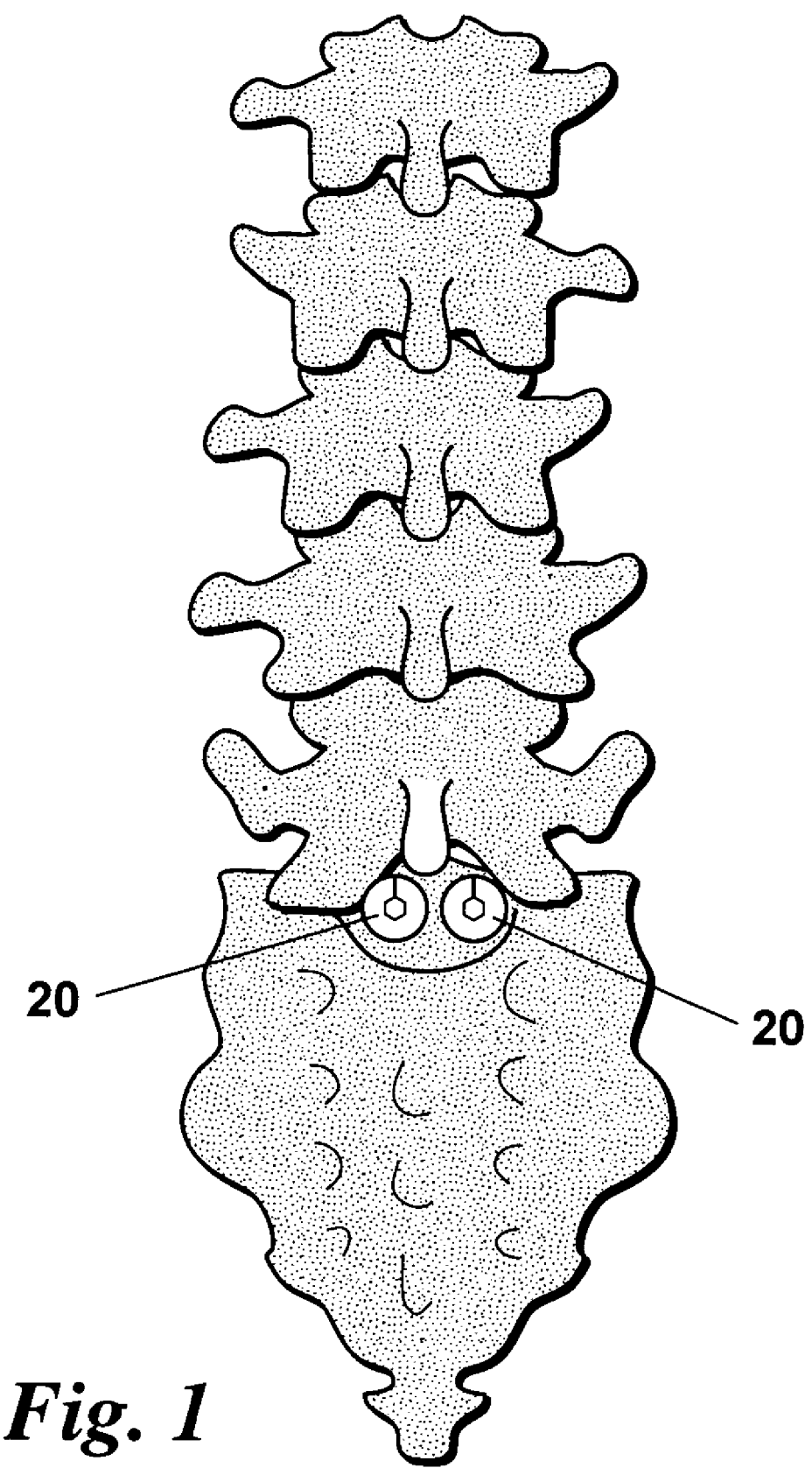
FIG. 1 anatomically illustrates a bilateral posterior insertion of two inventive spine fusion cages to achieve fusion across the L5/S1 disc space.

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

As used herein the phrases "bone growth inducing agent(s)," "bone growth agent(s)," "bone growth accelerant", "bone morphogenic protein(s)," and "BMP" refer synonymously to any substance useful in stimulating bone growth, whether a protein or not. Such substances are well known in the art.

As used herein the terms "carrier" and "carrier material" refer synonymously to any material capable of absorbing or otherwise holding or containing a bone growth inducing agent and which allows for the delivery of such agent to a target bone structure.

In the preferred embodiment of the present invention, a bone implantable device and carrier combination is implanted into the body prior to application of bone growth agent to the carrier. As indicated in the various example embodiments disclosed herein, the device may take a variety of forms. Typically, the device is made from titanium, alloys of titanium, Carbon fiber, bone or ceramic, but it may be made of any suitably strong material tolerated by the body. The device may comprise a unitary structure or may be of a multi-piece construction. In certain applications it may be advantageous to include a removable end cap or cover to allow access to the interior of the device. Further, the device or portions of the device, such as an end cap or other component may be constructed of a bio-absorbable material.

The device is preferably pre-loaded with carrier material, which may be retained in a hollow within the device or otherwise retained, such as adhesively, to an outside surface portion of the device. After the device and carrier combination is implanted, bone growth agent is applied to the carrier in a manner avoiding its contact with non-target body structures.

As bone growth agent is conventionally applied in liquid form, several preferred embodiments of the bone implantable device include a conveniently placed injection port that communicates with the carrier material. A plenum may be used to confine the flow of the bone growth agent from the injection port to the carrier material and to obtain even saturation of the material.

Besides enabling the better handling of the bone growth agent during the surgical procedure, the inventive bone implantable device better manages the stimulated bone growth by providing, in effect, one or more artificial tissue planes that prevent bony overgrowth in undesirable directions. The device allows bone growth agent to elute to the target bone structure, preferably through pathways or openings directly contacting the target bone structure, but the bone growth agent is otherwise confined in the device. The device walls prevent leakage of the bone growth agent toward sensitive areas or structures.

Bone implantable devices and implantation methodologies of the invention allow for the careful application of biologically active substances, such as bone growth accelerants including bone morphogenic proteins (BMP) for management of bone growth processes. Although bone growth accelerants are referred to in the below examples, it should be understood that the bone implantable devices of the invention may be used to deliver other biologically active substances as well. As will be discussed below, the bone implantable device of the invention may take the form of interbody spinal fusion cages, facet fusion screws, artificial joints, bone fixation plates, interbody grafts, e.g. intervertebral body grafts, IM nails, hip stems, and other orthopedic appliances where promoting bone-to-bone growth or growth from bone into the device is beneficial. Additionally, it is contemplated that the bone implantable devices of the invention may be used to deliver substances to enhance the growth of cartilage, tendon and other body structures in addition to bone.

The present invention will be further understood with reference to the following non-limiting examples.

EXAMPLE 1

Spine Fusion Cages

Several types of conventional spine fusion cages have been designed, such as those described by Bagby, Brantigan and Ray, respectively, in *Athrodesis by the Distraction-Compression Method Using a Stainless Steel Implant*, Orthopaedics 1988, Vol. 11:931-4; *A Carbon Fibre Implant to Aid Interbody Lumbar Fusion*, Spine 1991, 16 (Suppl):S277-82 (with Steffee and Geiger); and *Threaded Titanium Cages for Lumbar Interbody Fusions*, Spine 1997, 22:667-80; and as described in the patent art, for example, in U.S. Pat. Nos. 4,501,269; 5,055,104; 5,571,192; 5,702,449; 5,876,457; 5,906,616; 5,976,187; 5,980,522; 6,010,502; 6,015,436; and 6,039,762. Each of the foregoing publications and patents is incorporated herein by reference.

Such devices provide for a relatively simple and effective technique for implementing lumbar interbody fusion by correcting any existing mechanical deformity of the spine while providing stability and a good environment until successful arthrodesis is obtained. These cage devices are hollow and are positioned between the articulating vertebrae, where they support and immobilize the joint as well as contain the growth of the bone graft that is packed into the internal cavity of the device.

Anterior lumbar interbody fusion (ALIF) and posterior lumbar interbody fusion (PLIF) are two commonly adopted approaches for grafted lumbar interbody fusion with augmentation via a spine fusion cage. ALIF is performed through a retroperitoneal or transperitoneal approach with extensive discectomy followed by the placement of one or more cages in the vertebral interspace. In PLIF, partial or complete laminectomy and facetectomy is followed by posterior discectomy and the placement of one or more cages in the vertebral interspace. FIG. 1 is illustrative of a bilateral posterior insertion of two inventive spine fusion cages 20 to achieve fusion across the L5/S1 disc space. The cages 20 are secured far enough apart from each other (by a few millimeters) to avoid contact and potential back-threading. It should be understood that the fusion cages of this invention can be installed in their operative positions via either the anterior or posterior approaches; however, the posterior approach is the most dangerous in regards for bony overgrowth impinging on neural tissue particularly when the cage is used along with bone growth inducing materials.

The inventive cages 20 promote bony fusion by holding adjacent levels immobile and by allowing bone to grow only into the vertebral bodies an away from the spinal canal and nerve roots. Designs that do not control direction of growth are undesirable for use with biologic bone growth agents to the extent unchecked bony overgrowth may impinge upon neural tissues. Through the present invention there are provided designs for spine fusion cages which prevent bone growth around and into sensitive areas of neural tissue.

Figure 2:
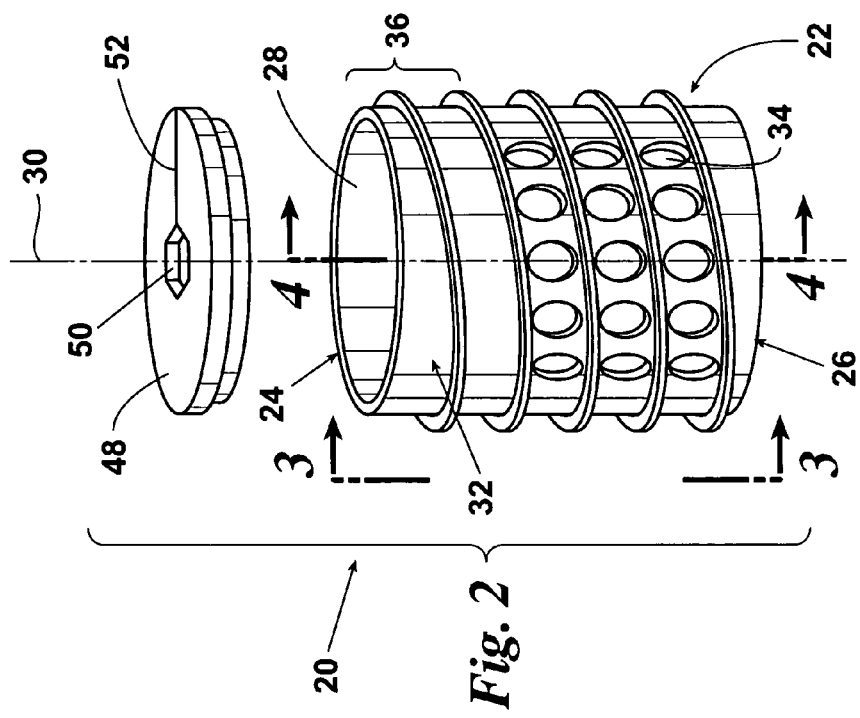
FIG. 2 is an exploded perspective view of an embodiment of an inventive cage having preselected perforated and non-perforated zones on its outer surface.
Figure 3:
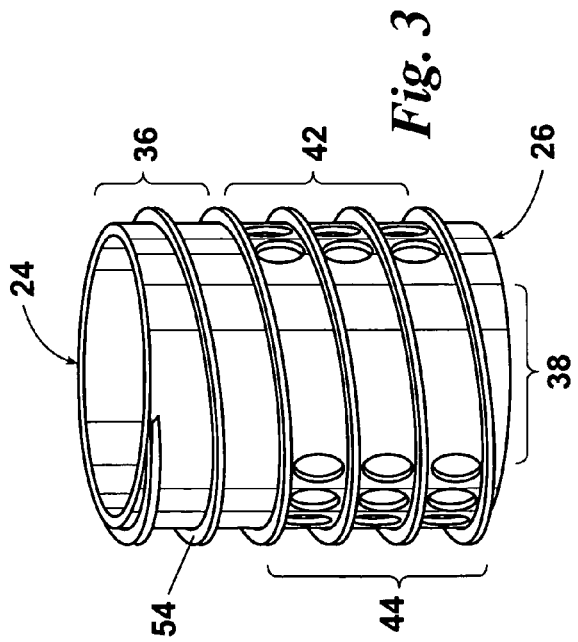
FIG. 3 is a perspective view taken along line 3-3 of FIG. 2.
Figure 4:
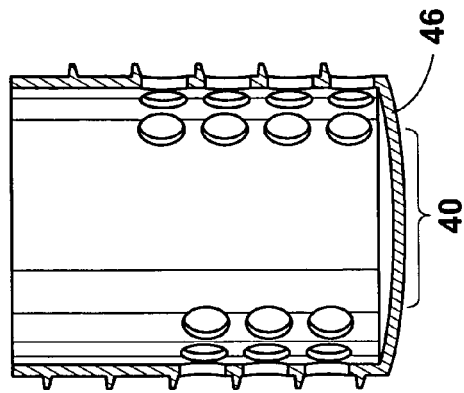
FIG. 4 is a sectional view taken along line 4-4 of FIG. 2.

Referring now to FIGS. 2-4, and in accordance with one embodiment of the present invention, there is provided an inventive spine fusion cage 20 wherein growth of bone into sensitive areas is prohibited by providing the cage with various zones or areas wherein the cage wall is either perforated or non-perforated. A cage body 22 is provided having a posterior end 24 and an anterior end 26 and defining an internal cavity 28 and a longitudinal axis 30. The cage body 22 is typically between 20-25 mm in length and may be of a variety of diameters, dimensions and heights. The cage body 22 has an outer surface 32 and a plurality of radial apertures 34 or pathways extending through the outer surface 32 in communication with the internal cavity 28 in a preselected pattern. Preferably, there is a first non-perforated zone 36 extending from the posterior end 24 of the cage body 22 a preselected length, preferably 5-10 mm, toward its anterior end 26, second and third non-perforated zones 38, 40 on the lateral sides of the cage body 22 extending in opposing relation from the first zone 36 further toward the anterior end 26, and two opposed perforated zones 42, 44 oriented cephalad (or to the superior side) and caudad (or to the inferior side) so that upon insertion of the device the perforated zones 42, 44 will be adjacent the vertebral bodies to be fused to allow bone growth across the vertebral interspace. Ends 24, 26 of the cage body 22 are provided with a non-perforated closure. In the illustrated embodiment, the anterior end 26 is closed by an integral non-perforated end wall 46, while there is provided a removable end cap 48 securable, by threaded attachment, friction fit or otherwise, to the posterior end 24 of the cage body 22. The end cap 48 may be provided with a recess 50 for receiving an insertion tool, for example if the end cap is made to threadably connect to the cage body, and there is preferably provided on the top of the end cap 48 a line score 52 for aiding proper orientation of the device in the vertebral interspace.

The cage body 22 may be provided with threads 54, projections, ridges, protrusions, barbs, spurs or other insertion means to aid in placement of the cage within the interbody area. The anterior end 26 can be rounded in order to facilitate the insertion of the cage 20 relative to one or more bone structures. The cage 20 may be made of surgical steel, titanium or other acceptable implantable materials. Typically, the cage 20 is countersunk into the vertebral interspace with the end cap 48 in place by using an insertion tool (not shown) to screw the cage 20 into position. Once the cage is properly aligned, the end cap 48 is removed so that bone growth inducing material can be packed into the internal cavity 28 of the cage body 22, whereupon the end cap 48 is tightly replaced.

As can now be appreciated, the inventive cage 20 prevents bone growth into areas adjacent the non-perforated zones when the fusion cage is in place. Because the posterior 5-10 mm of the cage is non-perforated, including, importantly, the end cap, bony overgrowth is inhibited in areas immediately adjacent the posteriorly located neural tissues. In similar fashion, lateral overgrowth of bone is impeded by the second and third non-perforated zones. Desired growth through the vertebral interspace, however, is facilitated via the perforated zones.

It should be understood to be within the ordinary skill of one in the art to modify the placement of the various perforated and non-perforated zones as warranted by orthopaedic considerations to achieve desired bone growth and preclude unwanted bone growth. It is also within the ordinary skill of one in the art to modify the aforedescribed device for anterior insertion procedures by providing a removable end cap on the anterior end of the cage body and reversing the thread direction on the outside surface of the cage body.

As mentioned above, it is also advantageous for a surgeon to have the ability to selectively occlude apertures in the cage wall to prevent bone growth in undesired directions. Now referring to FIGS. 5-8, to achieve this object, and in accordance with another embodiment of the present invention, there is provided a spine fusion cage 120 having an outer cage body 122 with a posterior end 124 and an anterior end 126 and defining an internal cavity 128 and a longitudinal axis 130.

The outer cage body 122 has an outer surface 132 and a plurality of radial apertures 134 extending through the outer surface 132 in communication with the internal cavity 128 in a pattern covering a substantial portion of the outer surface 132 of the cage body 122. An inner cage body 136 into which is placed bone growth inducing substances is disposed within the internal cavity 128 of the outer cage body 122 and is positioned as to form an annulus 138 between the inner wall surface 140 of the outer cage body 122 and the outer wall surface 142 of the inner cage body 136. The inner cage body 136 likewise has a plurality of radial apertures 144 extending through its outer surface 142 so as to establish communication with the annulus 138 and the outer surface 132 of the outer cage body 122. A solid end closure 146 having opposed occluding surfaces 148, 150 suitable for introduction into the annulus 138 serves to establish one or more desired zones or patterns of occluded apertures amongst the plurality of apertures in the outer cage body 122, thereby obstructing bone growth in undesired directions.

Figure 5:
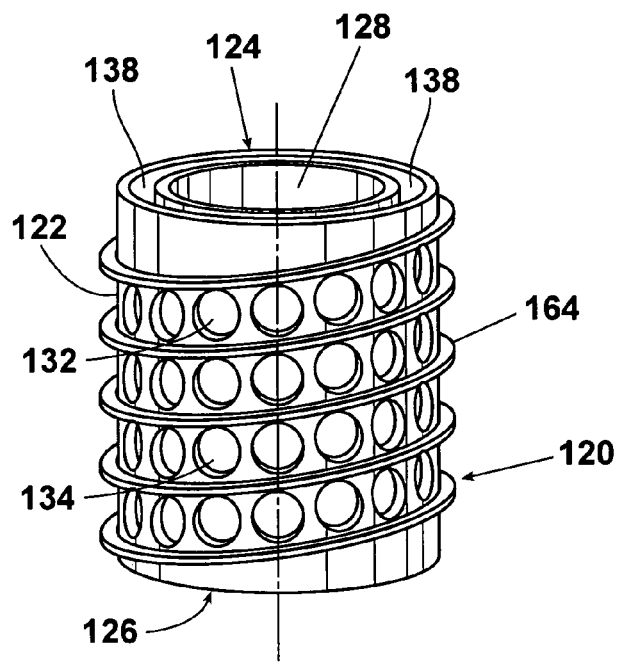
FIG. 5 is perspective view of an embodiment of an inventive cage having outer and inner cage elements.
Figure 6:
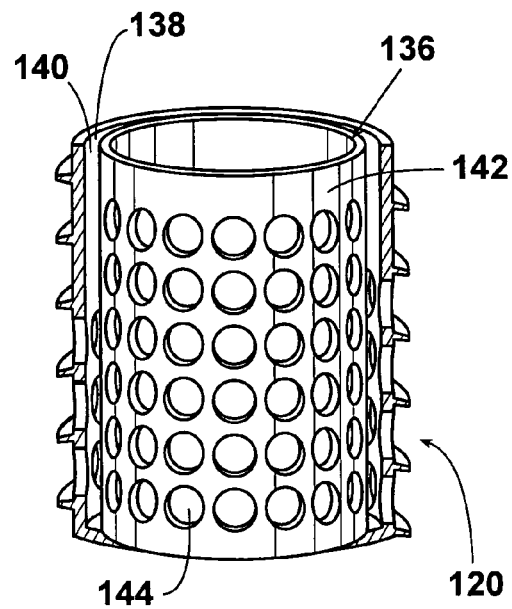
FIG. 6 is a sectional view taken along line 6-6 of FIG. 5.
Figure 7:
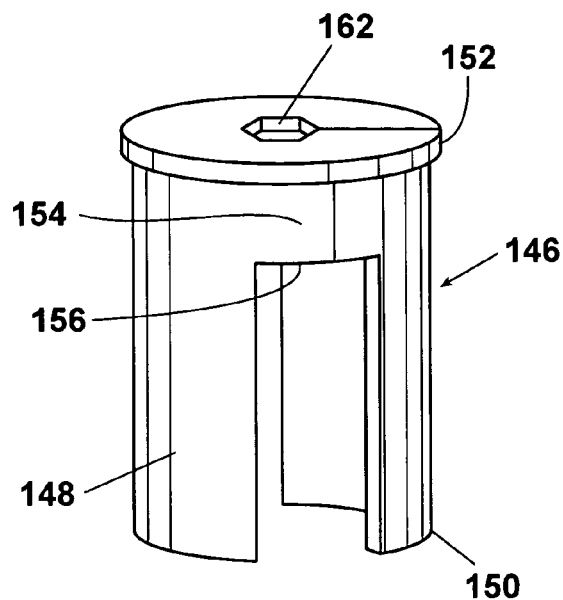
FIG. 7 is a perspective view of an end closure for use in connection with the cage of FIG. 5.
Figure 8:
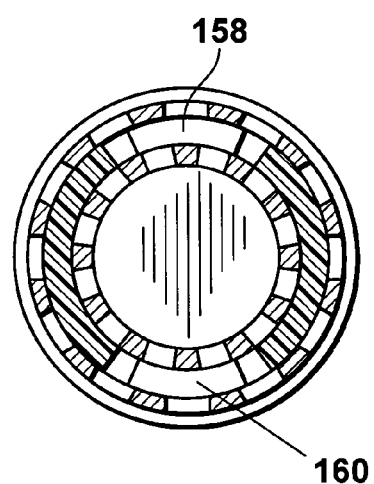
FIG. 8 is a top sectional view of the cage of FIG. 5 including the end closure of FIG. 7.

More specifically, as shown in FIG. 7 end closure 146 is comprised of a non-perforated cap or closure means 152 having occluding surfaces 148 and 150 extending therefrom. Such surfaces may be of sufficient length to extend to the bottom of the cage member 120 as shown in FIG. 5 or may be of a more limited length so as to occlude only a portion of the apertures 134 in the outer cage body 122. The end closure 146 may be constructed so as to provide a top circumferential crown portion 154 and between the occluding surfaces 148, 150 a shoulder 156 which may engage a rib means 158, 160 as shown in FIG. 8 to act as a longitudinal stop and to limit the degree of rotation which can be made by occluding surfaces 148, 150 so as to maintain the selected occlusion pattern. When positioned within the annulus 138 of the fusion cage 120, the occluding surfaces 148, 150 serve to close openings in the posterior end of the cage 120 as well as to occlude openings or pathways which are in a lateral position so as to effect bone growth through the apertures in the caudal and cephalad directions when placed in the desired position between two vertebrae. Various interchangeable forms of end closures may be provided, for example having differently shaped and dimensioned occluding surfaces, so as to provide for the surgeon a selection which meets objectives according to various orthopaedic exigencies. It is also within the scope of this invention that the shape and dimensions of the occluding surfaces may be modifiable by the surgeon, such as if the occluding surfaces comprise a surgical plastic adapted to be cut or trimmed to achieve a desired configuration. In this manner, a cage possessing a full pattern of apertures can be used as a "universal" cage in combination with one of a wide selection of end closures or a modifiable end closure to achieve any desired patterned of perforation.

The end closure 146 can be threaded or otherwise designed to effect the closure of the posterior end of the cage 120 and may be provided with securing means such as square or hex-shaped recess 162 which can be used with a socket wrench to tightly position the end closure 146 in the posterior end of the fusion cage 120. In complementary fashion, threads may be provided at the posterior end of the cage 120 to receive a threaded end closure 146 or it can be so adapted that the end closure 146, when not threaded, can be simply snapped into place to effect the desired closing of the fusion cage 120.

A thread 164 may be provided as part of the outer surface 132 of the fusion cage 120. Such a thread can be replaced with a plurality of discrete threads or a plurality of projections, ridges, protrusions, barbs or spurs and be within the spirit and scope of the invention.

In assembly of the fusion cage of this embodiment of the invention, following introduction of the selected biologic material into the internal cavity 128 within the inner cage body 136, the annulus 138 remains clear so as to easily accept end closure 146 within the annulus 138 while the biologic materials are retained in the internal cavity 128. Through the dimensioning, shaping and rotation of occluding surfaces 148, 150 there is achieved an occlusion of apertures so as to define the desired pattern of apertures through which bone growth is to be permitted.

In keeping with the teachings of the present invention, there is further provided a novel closure for conventional spine fusion cages which can be used with little or no modification to presently available fusion cages in preventing bone growth into undesirable areas. This embodiment involves providing a means for the occlusion of selected apertures in currently available fusion cages, such as to those commonly referred to as Brantigan, BAK and Ray cages, so that bone growth is directed only toward the vertebral bodies and away from the spinal canal and nerve roots.

Figure 9:
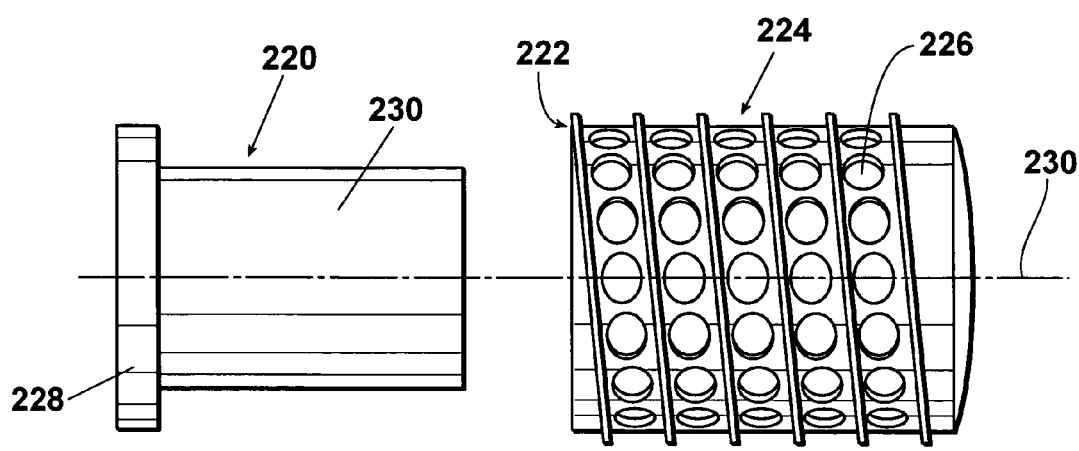
FIG. 9 is an exploded side view of a conventional fusion cage modified to utilize an inventive end closure means to selectively occlude certain apertures in the outer surface of the cage.
Figure 10:
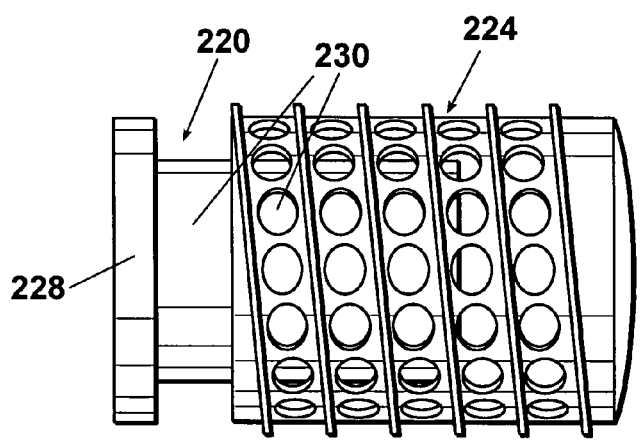
FIG. 10 depicts the partial insertion of the inventive closure means into the cage of FIG. 9.
Figure 11:
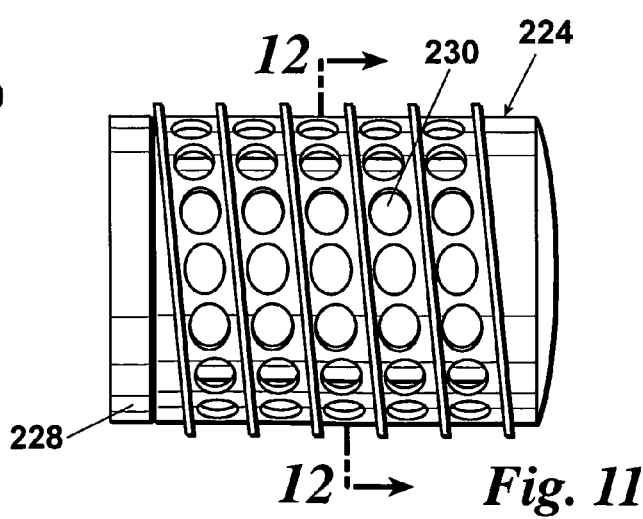
FIG. 11 depicts the full insertion of the inventive closure means into the cage of FIG. 9.

Making reference now to FIGS. 9-11, there is illustrated an end closure 220 for effecting the closure of the posterior end 222 of a conventional fusion cage body 224 while establishing a desired occlusion pattern of apertures in the wall of the cage body 224, which cage possesses apertures 226 substantially entirely thereabout. The end closure 220 comprises a non-perforated sealing member 228 to effect the closure of the posterior end 222 of the cage body 224 and one or more occluding surfaces 230, 231 extending from the sealing member 228 essentially parallel to the longitudinal axis 230 of the cage body 224 so as to establish one or more desired zones or patterns of occluded apertures amongst the plurality of apertures in the cage body 224. Reference is made to the disclosure provided above with respect to the aforedescribed end closure 146, which disclosure is equally applicable to end closure 220 and further recitation is believed unnecessary. Suffice it to say that the prior described end closure 146 may be made adaptable to conventional fusion cages so as to achieve the objectives of the present invention.

Figure 12:
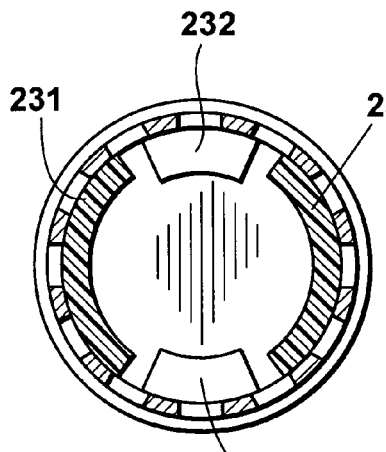
FIG. 12 is top sectional view of a modified conventional cage including an inventive end closure means.

As depicted in FIG. 12, if desired the conventional type of fusion cage can be so modified as to provide ribs 232, 234 in association with the inner surface of the posterior end of the cage according to the teachings herein. FIG. 12 provides a top view of the fusion cage of FIG. 11 along the line 12-12 which shows the placement of the ribs 232 and 234 to accommodate occluding surfaces 230, 231 of the end closure 220.

Referring now to FIG. 13, an exploded view of an embodiment of an inventive cage 300 is shown having an end cap 302 and an end cap 304 having an orifice 306. Orifice 306 is preferably sealed with a plug 308, e.g. a silicone plug or a plug of another material capable of being penetrated by a syringe needle to dope a carrier 310. Carrier 310 is provided to receive bone growth accelerants, such as bone morphogenic proteins, and is located in the interior of cage 300. A preferred carrier 310 is a sponge type material such as bovine collagen sponge or any type of collagen that will bind to bone growth accelerant. In use, the cage 300 is desirable because cage 300 may be located within a patient prior to loading cage 300 with bone growth accelerants. Locating cage 300 prior to loading the bone growth accelerant prevents bone growth accelerant from inadvertently contacting areas of the patient that are not intended to experience bone growth. After the cage 300 is located, bone growth accelerant may be carefully administered via a syringe needle, which is pushed through plug 308. Once the syringe needle has penetrated plug 308, bone growth accelerant may be delivered to the carrier 310, e.g. sponge material. By doping the carrier material 310 in this way, the risks associated with locating a cage 300 filled with bone growth accelerant are minimized. Additionally, the bone growth accelerant may be pre-loaded onto the carrier material 310 in a dissolvable form, e.g., a crystalline form, gel or other form that will eventually migrate outside of cage 300 once implanted into a human body and exposed to body fluids, body heat, etc. Of course, a dissolvable form of carrier material may be utilized in any of the examples of the invention as desired.

Figure 28:
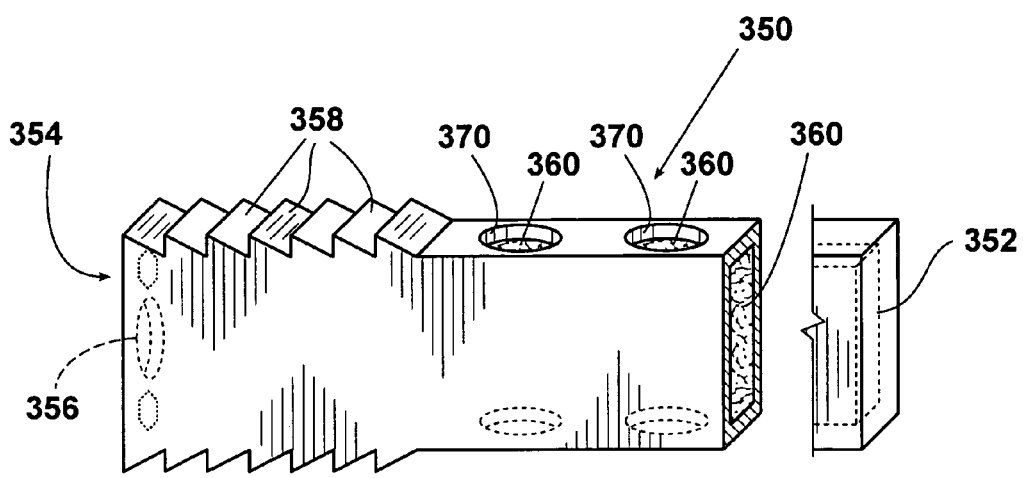
FIG. 28 is a perspective view of another embodiment of the spinal fusion cage.

Referring now to FIG. 28 a partial cross-sectional view of a rectangular embodiment of an inventive cage 350 is shown having a first end 352 and a second end 354. Second end 354 defines an orifice 356. Splines 358 are provided to assist in securing cage 350 in a desired location. Orifice 356 is preferably sealed with a plug, e.g. a silicone plug or a plug of another material capable of being penetrated by a syringe needle to dope a carrier material 360. Holes 361 are used to manipulate cage 350 during placement of cage 350. Carrier 360 is provided to receive bone growth accelerants, such as bone morphogenic proteins, and is located in the interior of cage 350. A preferred carrier 360 is a sponge type material such as bovine collagen sponge or any type of collagen that will bind to bone growth accelerant. In use, the cage 350 may be located within a patient prior to loading cage 350 with bone growth accelerants. Locating cage 350 prior to loading the bone growth accelerant prevents bone growth accelerant from inadvertently contacting areas of the patient that are not intended to experience growth. After the cage 350 is located, bone growth accelerant may be carefully administered through orifice 356. Preferably, bone growth accelerant is delivered via a syringe needle, which is pushed through a plug located within orifice 356. Once the syringe needle has penetrated the plug, bone growth accelerant may be delivered to the carrier 360, e.g. sponge material. By doping the carrier material 360 in this way, the risks associated with locating a cage 350 filled with bone growth accelerant are minimized. Additionally, bone growth accelerant may be pre-loaded onto the carrier material 360 in a dissolvable form, e.g., a crystalline form, gel or other form that will eventually migrate outside of cage 350 once implanted into a human body and exposed to body fluids, body heat, etc. Bone growth accelerant passes through pathways or orifices 370 to contact target bone material.

Figure 19:
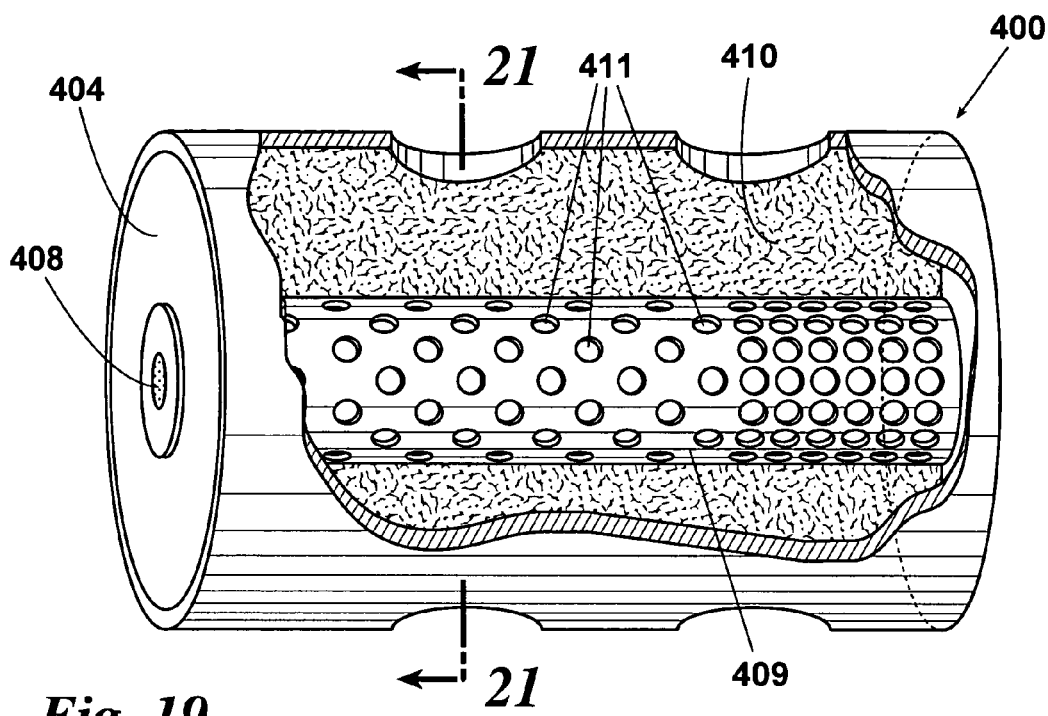
FIG. 19 is a partial cross-sectional view of a bone implantable structure for use as a spinal fusion cage wherein the spinal fusion cage has a plenum member located therein.
Figure 20:
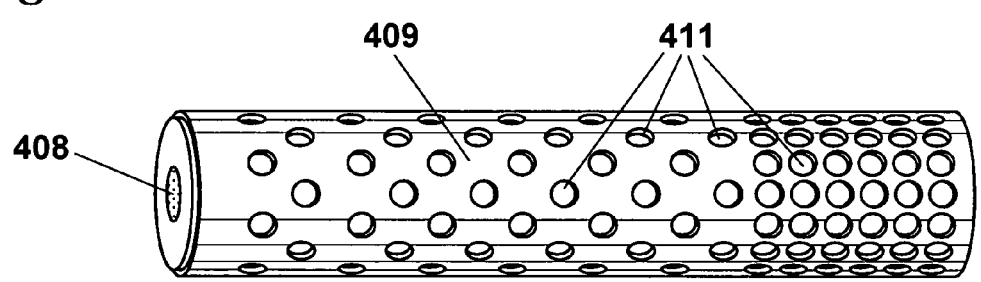
FIG. 20 is a perspective view of the plenum member of FIG. 19.
Figure 21:
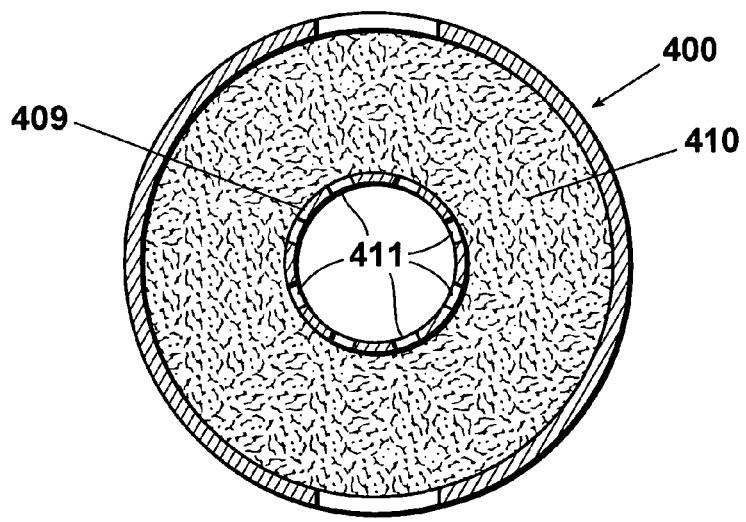
FIG. 21 is a cross-sectional view taken along line 21-21 of FIG. 19.
Figure 29:
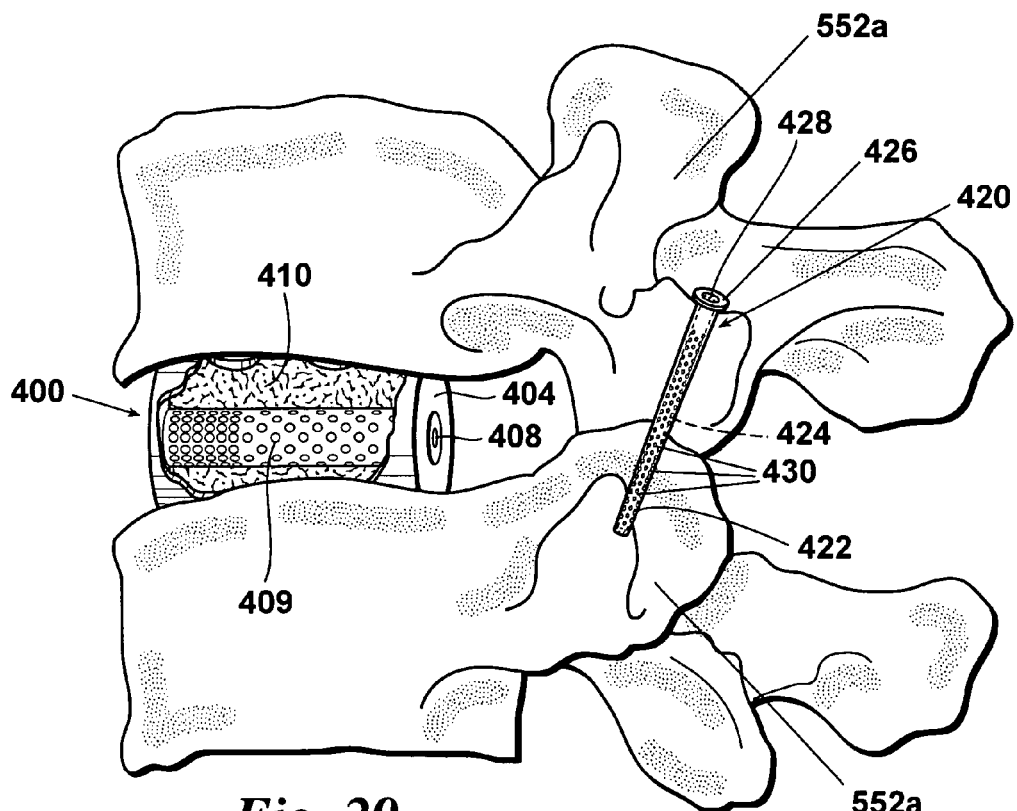
FIG. 29 is a partial cross-sectional view of a "360° fusion" vertebral fusion including the spinal fusion cage of FIG. 19 and a facet fusion screw engaging adjacent vertebral facets.

As a further example of a bone implantable device of the invention, an exploded view of an embodiment of an inventive cage 400 is shown in FIGS. 19 and 21 having an end cap 404 defining an orifice. The orifice is preferably sealed with a plug 408, e.g. a silicone plug or a plug of another material capable of being penetrated by a syringe needle. A carrier 410 for a bone growth accelerant, such as bone morphogenic protein, is located in the interior of cage 400. A preferred carrier 410 is compatible with a bone growth or biologic agent and holds and dispenses the agent in a time released and controlled fashion. An example of a suitable carrier 410 is a bovine collagen material. In use, the cage 400 may be located within a patient prior to loading cage 400 with bone growth accelerants. Placement of cage 400, e.g., between adjacent vertebra as shown in FIG. 29, prior to loading the bone growth accelerant prevents bone growth accelerant from inadvertently contacting areas of the patient that are not intended to experience bone growth. After the cage 400 is located, bone growth accelerant may be carefully administered through the orifice defined by end cap 404. A preferred method is via a syringe needle, which is pushed through plug 408. Once the syringe needle has penetrated plug 408, bone growth accelerant may be delivered into plenum 409, which assists in evenly distributing the bone growth accelerant to the carrier 410, i.e.,
assists in doping carrier 410. As shown in FIGS. 19 and 20, plenum 409 is provided with a plurality of pathways or orifices 411 though which the bone growth accelerant may migrate into carrier 410. Preferably, orifices 411 are distributed over the length of plenum 409 such that a greater concentration of orifices may be found on an end of the plenum opposite plug 408. The unequal distribution of orifices 411 over the length of plenum 409 is designed to compensate for a disparity in the amount of bone growth accelerant delivered into the plenum 409. Alternatively, orifices 411 may be smaller at one end and larger at an end of the plenum 409 opposite plug 408. In either case, an orifice area near an end of the plenum 409 opposite plug 408 is preferably greater than an orifice area on plenum 409 nears plug 408. The desired result is for the bone growth accelerant to migrate into carrier 410 in a uniform distribution over the length of carrier 410.

Referring now to FIG. 29, a transarticular screw, such as facet fusion screw 420 is shown as yet another example of a bone implantable device of the invention. Facet fusion screw 420 is constructed of body 422, which defines a carrier receiving area 424. An end cap may be provided to seal the carrier receiving area, such as upper end cap 426. Upper end cap 426 is preferably provided with an injection port 428 to facilitate delivery of bone growth accelerant onto a carrier material for doping the carrier material that has been located within the carrier receiving area 424. Pathways or orifices 430 are provided in a location adjacent to vertebral facets 552a. Bone growth accelerant located within the carrier receiving 424 area migrates outwardly through pathways 430 into contact with adjacent vertebral facets 552a and promotes bone growth through pathways 430 to secure facet fusion screw 420 to the vertebrae, thereby immobilizing adjacent vertebrae with respect to one another. Facet fusion screw 420 is shown being used in combination with spinal fusion cage 400 discussed above, to achieve a "360° fusion" of adjacent vertebrae 552. Although facet fusion screw is shown being used with spinal fusion cage 400, use of facet fusion screw 420 with other spinal fusion cages is also contemplated.

Figure 18:
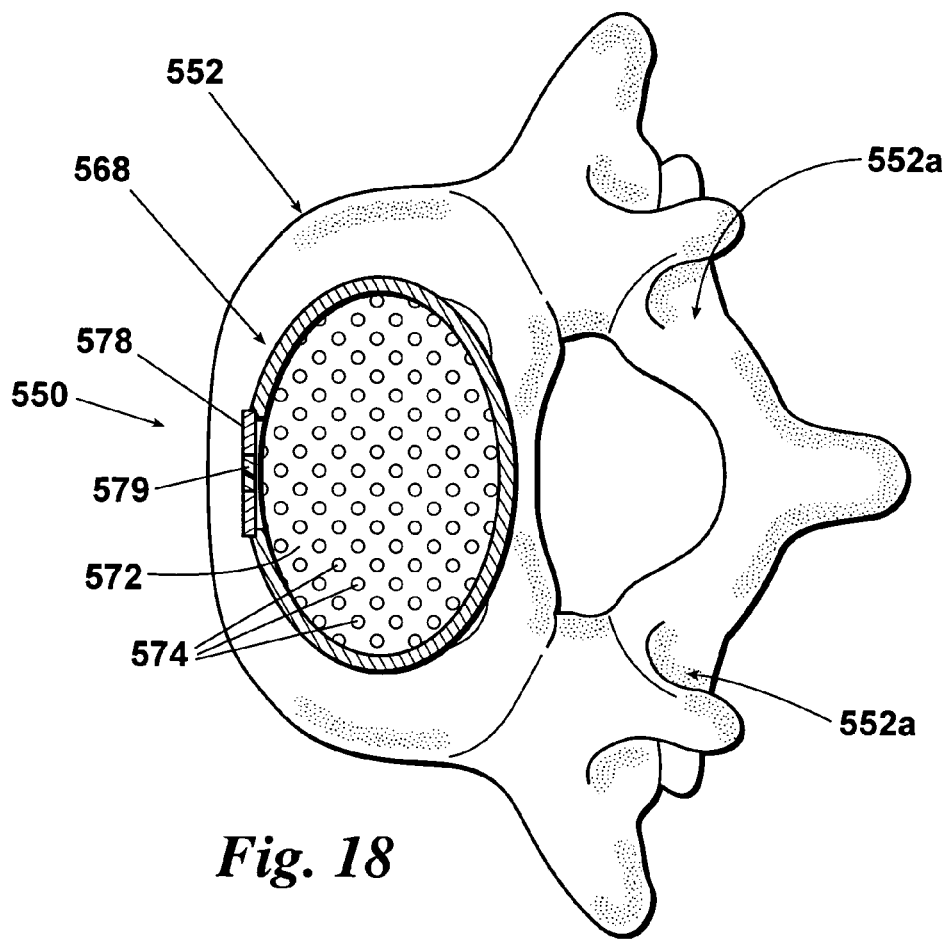
FIG. 18 is a cross-sectional view taken along lines 18-18 of FIG. 17.
Figure 17:
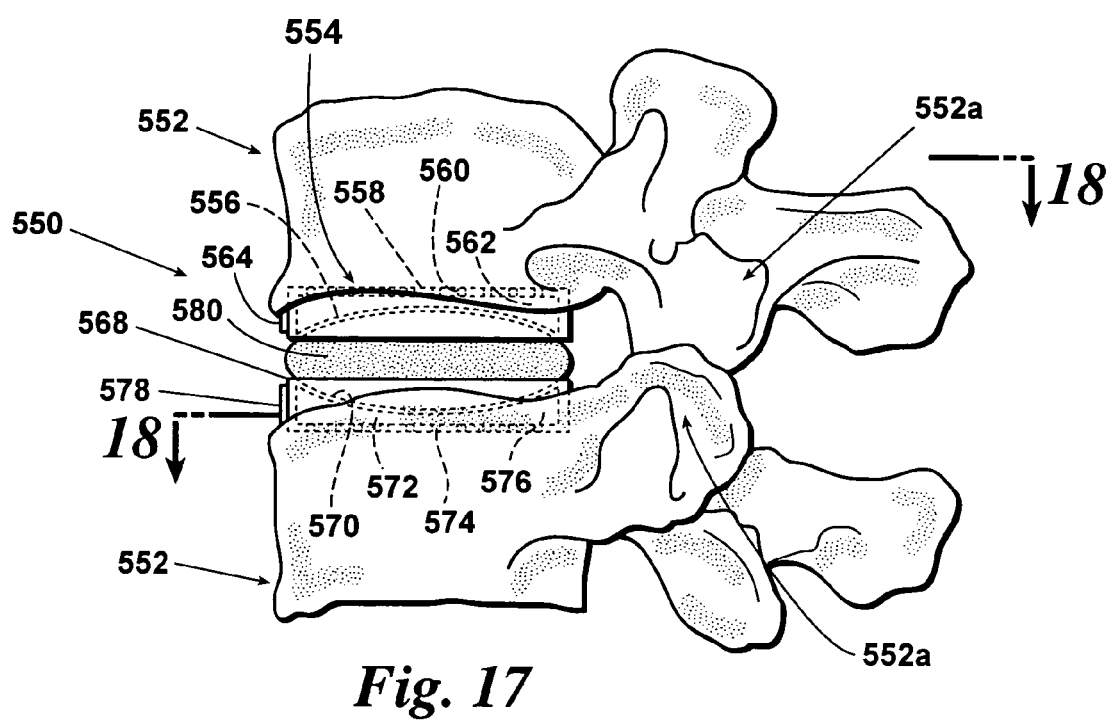
FIG. 17 is a side view of an artificial joint fused to adjacent vertebrae.

In addition to the interbody spinal fusions cages discussed above, further embodiments of applicant's bone implantable device invention may take the form of a an IM nail 450 (FIG. 14), hip stem 500 (FIGS. 15, 16), artificial disk assembly 550 (FIGS. 17, 18), interbody graft 650 (FIGS. 22-24), bone fixation plates 700 (FIGS. 25-27), and other orthopedic appliances where promoting bone-to-bone growth or growth from bone into the device is beneficial.

EXAMPLE 2

IM Nails

Figure 14:
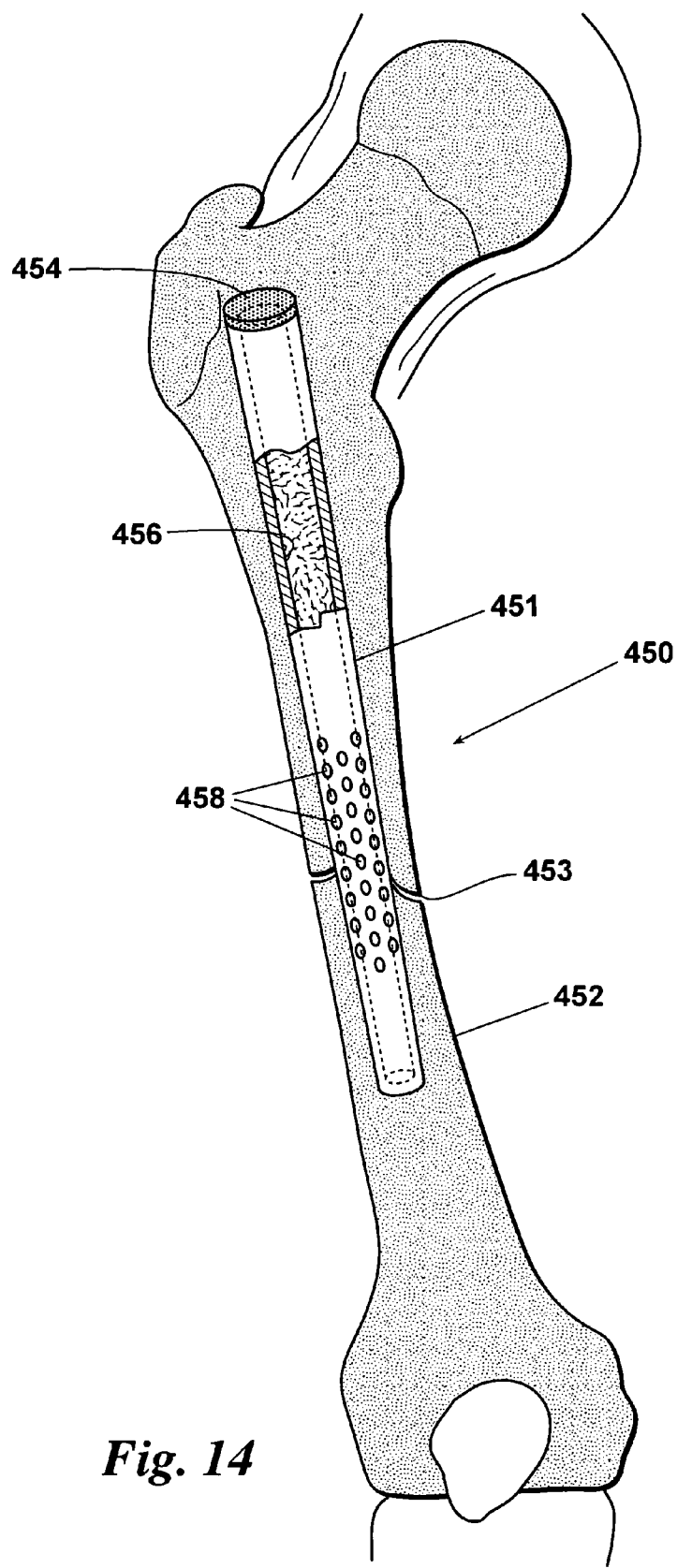
FIG. 14 is a partial cross-sectional view of an embodiment of a bone implantable device shown located within a bone structure.

Referring now to FIG. 14, IM nail 450 is shown located in an interior cavity of femur 452. Femur 452 is shown with break 453. IM nail 450 has a body 451 and an end cap 454 that encloses carrier receiving area 456. Without end cap 454, a port is accessible for doping carrier material located in carrier receiving area 456. A plurality of pathways or orifices 458 communicates carrier receiving area 456 with an exterior of body 451. Preferably, IM stem 450 is carefully selected so that, upon placement within femur 452, orifices 458 are located adjacent break 453. By loading carrier receiving area 456 with a carrier and bone growth agent and locating orifices 458 adjacent break 453, improved mending of break 453 is facilitated.

EXAMPLE 3

Hip Stems

Figures 15, 16:
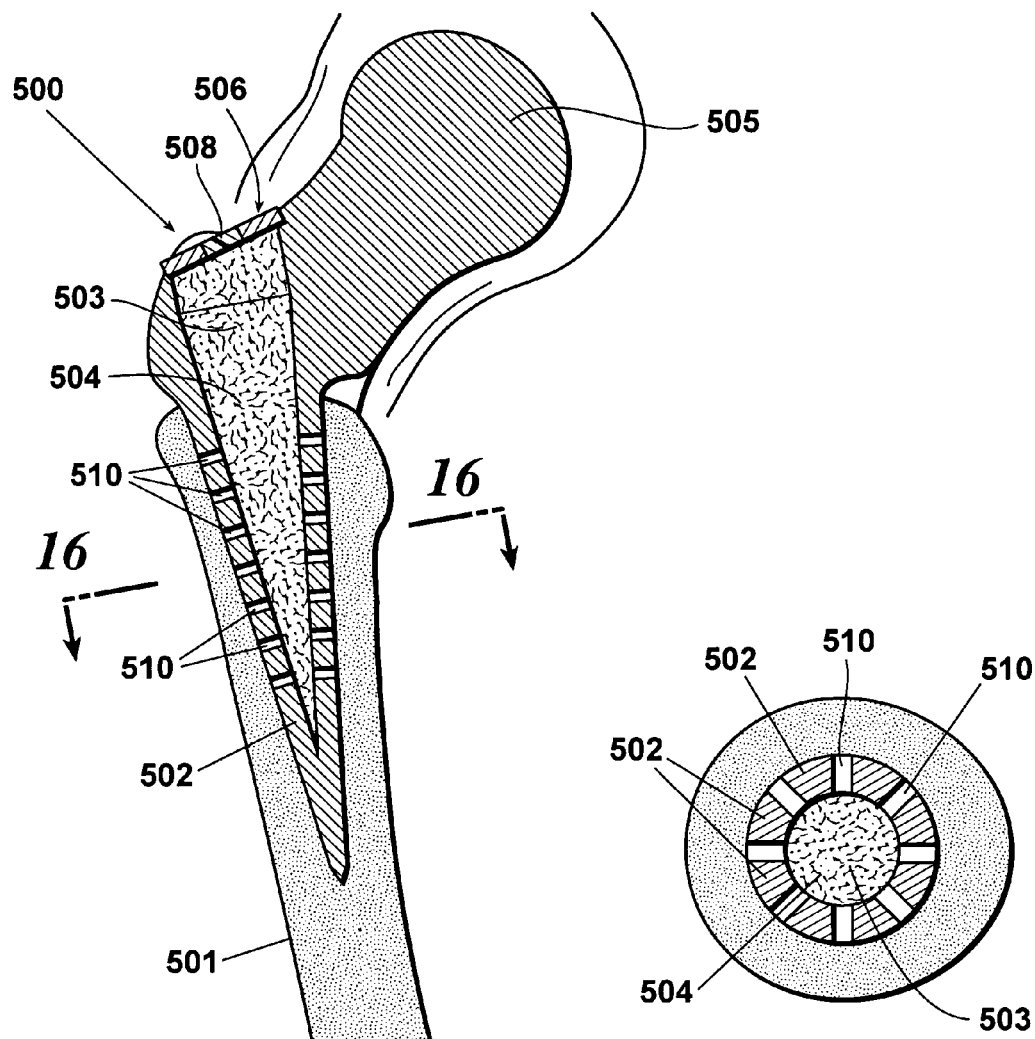
FIG. 15 is a cross-sectional view of an embodiment of a bone implantable structure shown functioning as a ball portion of a ball and socket joint.
FIG. 16 is a cross-sectional view of the embodiment of FIG. 15 taken along line 16-16 of FIG. 15.

Additionally, the bone implantable device of the invention may be fashioned into hip stem 500 (FIGS. 15, 16). Hip stem 500 is shown located in one end of a femur 501. Hip stem 500 has a body 502 defining a carrier receiving area 504 and a ball joint 505. Preferably, carrier receiving area 504 is accessible via end cap 506. End cap 506 is provided with injection port plug 508 for doping the carrier material. Carrier receiving area 504 is provided to receive a carrier 503 for bone growth agent. Pathways or orifices 510 allow bone growth agent to migrate from carrier receiving area 504 to an outside surface of body 502. Additionally, bone growth will propagate through orifices 510 to assist in securing hip stem 500 within femur 501.

EXAMPLE 4

Artificial Disks

Referring back to FIGS. 17 and 18, an artificial disk assembly 550 is shown between two adjacent vertebrae 552. Artificial disk assembly 550 includes an upper disk member 554 having a concave lower surface 556 and a perforated upper surface 558. Perforated upper surface 558 has a plurality of pathways or orifices 560 formed therein. Preferably, upper disk member 554 defines a carrier receiving area 562. Carrier receiving area 562 is accessible via a cap member 564. Preferably, cap member 564 is provided with an injection port plug to facilitate doping of carrier material. Artificial disk assembly 550 additionally includes lower disk member 568 having a concave upper surface 570 and a perforated lower surface 572. Perforated lower surface 572 has a plurality of pathways or orifices 574 (FIG. 18) formed therein. Preferably, lower disk member 568 defines a carrier receiving area 576. Carrier receiving area 576 is accessible via a cap member 578, which preferably receives an injection port plug 579 (FIG. 18) through which the carrier material may be doped. Concave surfaces 556 and 570 slidingly engage curved surfaces of artificial spinal disk 580, which is preferably constructed of a polymer or other suitable material. Perforated surfaces 558 and 572 are located adjacent respective vertebrae 552. Once a bone growth accelerant is injected onto carrier material located within carrier receiving areas 562 and 576, or as pre-loaded dissolvable carrier material is dissolved, the bone growth accelerant migrates into contact with vertebrae 552. Bone material is then stimulated to grow through orifices 560 and 574 to secure the upper disk member 554 and lower disk member 568 to adjacent vertebrae 552.

EXAMPLE 5

Interbody Grafts

Figure 22:
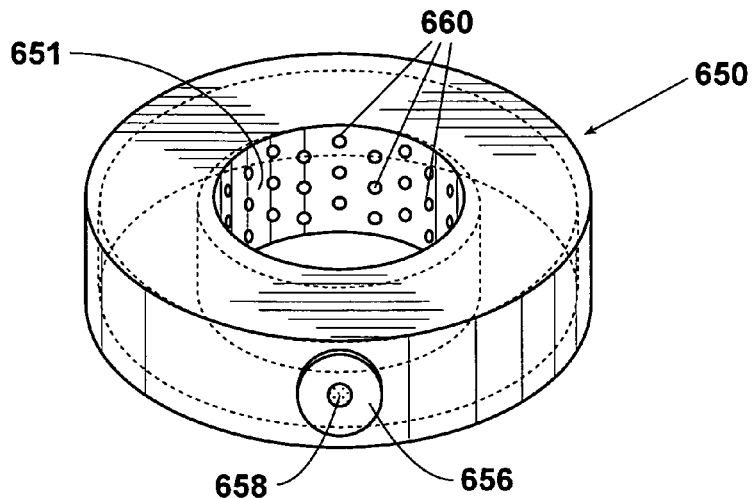
FIG. 22 is a perspective view of a bone implantable structure for use as an intervertebral body graft.
Figure 23:
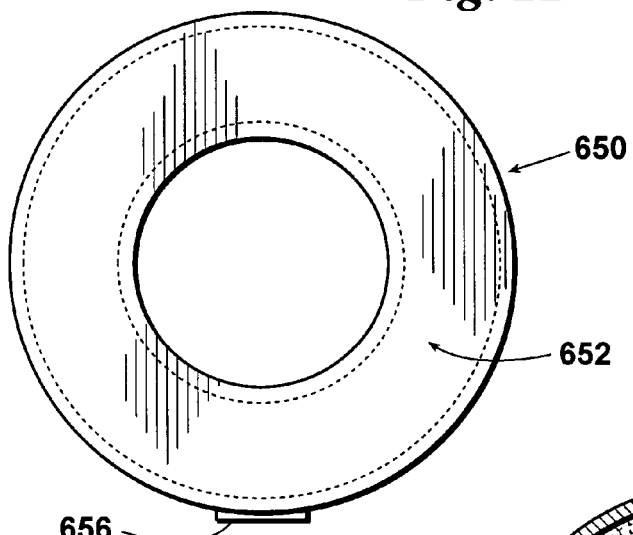
FIG. 23 is a top view of the intervertebral body graft of FIG. 22.
Figure 24:
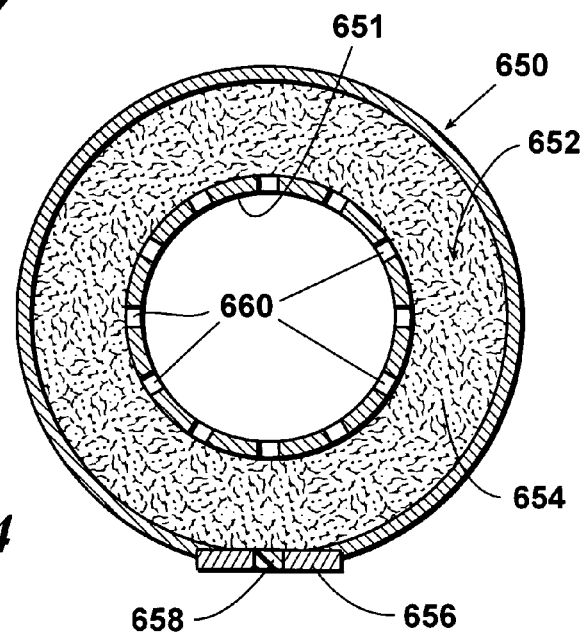
FIG. 24 is a cross-sectional view of the intervertebral body graft of FIG. 22.

As a further example of a bone implantable device, an interbody graft 650 is shown in FIGS. 22-24. Interbody graft 650 may be inserted between adjacent vertebrae to facilitate fusion of the vertebrae. Interbody graft 650 is constructed of a ring shaped body defining an inner surface 651 and an annular carrier receiving area 652 for receiving carrier material 654. Cap 656 is provided to access carrier receiving area 652. Preferably, cap 656 is provided with an injection port 658 for facilitating doping carrier material 654, i.e., for facilitating delivery of bone growth accelerant material onto carrier material 654. A plurality of pathways or orifices 660 are provided on inner surface 651 for delivery of bone growth accelerant to adjacent bone material. As the bone growth accelerant passes through orifices 660, adjacent bone structures are stimulated to grow into the opening defined by inner surface 651 where the two vertebrae fuse to one another.

EXAMPLE 6

Bone Fixation Plates

As shown in FIGS. 25-27, a bone fixation plate 700 is another example of a bone implantable device of the invention. Bone fixation plate 700 may be used to assist in mending broken bones, such a collar bone 701. Bone fixation plate 700 is provided with screw orifices 702 for receiving screws 704. Screws 704 are used to affix bone fixation plate 700 to bone 701. Bone fixation plate 700 defines a carrier receiving area 706, which may be a hollow area within bone fixation plate 700 or may be a recessed area defined by bone fixation plate 700 as shown most clearly in FIG. 27. Carrier receiving area 706 is provided to receive carrier material 708 (FIG. 25) and to position carrier material 708 adjacent a desired bone structure. In this embodiment, carrier receiving area 706 also functions as a pathway to facilitate the delivery of bone growth accelerant to the bone structure. An injection port 712 may be provided to access carrier receiving area 706 so that bone growth accelerant may be carefully administered to the carrier after implantation of bone fixation plate 700, i.e., so that the carrier material 708 can be doped.

In each of the above described examples, a conveniently placed injection port provides the ability to deliver bone growth accelerant in a manner that reduces potential contact with non-target bone structures. The injection port is preferably located on the device body and communicates with a carrier material located in the carrier receiving area. The injection port facilitates delivery of bone growth accelerant to the carrier after implantation of the device. Alternatively, avoiding inadvertent contact with non-target bone structures may be achieved in each of the above examples by pre-loading devices with a dissolvable form of bone growth accelerant that liquefies after exposure to an implanted environment.

Preferably, the bone implantable device includes a carrier receiving area that may be a hollow interior structure in which carrier material is located. When utilizing an injection port, bone growth accelerant is injected into the carrier material through an injection port after implantation of the device. One or more apertures communicating with the carrier receiving area may be located on a portion of the device that is, upon implantation, adjacent target bone structure, which allows for controlled delivery of bone growth accelerant to the target bone structure. A plenum may be provided in the carrier receiving area in an interior of the bone implantable device to facilitate the even distribution of bone growth accelerant from the injection port into the carrier material.

While the discussion has focused primarily on methods and devices for accelerating bone growth, it is contemplated that the devices and methods of the invention may also be used to deliver agents to other body structures including tendons and ligaments.

Finally, although the facet type screws discussed herein are shown facilitating the fusion of vertebral facets, it should be understood that the screws discussed herein may be useable in other ways and to fuse other bone structures besides vertebral facet structures discussed herein.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. An interbody spine fusion cage for fusing adjacent vertebrae, said spinal fusion cage comprising:
    a cage body defining an outside surface;
    a carrier receiving area defined by said cage body;
    an un-doped carrier material loaded in said carrier receiving area;
    a port that communicates said outside surface with said carrier receiving area for facilitating delivery of a biologically active substance onto said un-doped carrier material;
    a pathway that communicates with said carrier receiving area for delivering said biologically active substance from said carrier receiving area to a target bone structure;
    an end cap on an end of said cage body for enclosing said carrier receiving area;
    wherein said port is located in said end cap; and further comprising:
    a plug in said port adapted to be penetrated by a delivery device.

2. An interbody spine fusion cage according to claim 1 wherein:
    said delivery device is a syringe.

3. An implantable device for locating within a body, said implantable device comprising:
    a body defining an outside surface;
    a carrier receiving area defined by said body;
    an un-doped carrier material loaded in said carrier receiving area;
    a port that communicates said outside surface with said carrier receiving area for facilitating delivery of a biologically active substance onto said un-doped carrier material;
    a pathway that communicates with said carrier receiving area for delivering said biologically active substance from said carrier receiving area to a target bone structure;
    a plug in said port adapted to be penetrated by a syringe; and
    the interbody spine fusion cage further comprising:
        a substantially solid end cap on an end of said cage body wherein said end cap encloses said carrier receiving area; and
        wherein said port is located in said end cap.

4. An interbody spine fusion cage for fusing adjacent vertebrae, said spinal fusion cage comprising:
    a cage body defining an outside surface;
    a carrier receiving area defined by said cage body;
    an un-doped collagen carrier material loaded in said carrier receiving area;
    a port that communicates said outside surface with said carrier receiving area for facilitating delivery of a biologically active substance onto said un-doped carrier material;
    a pathway that communicates with said carrier receiving area for delivering said biologically active substance from said carrier receiving area to a target bone structure;
    a plug in said port adapted to be penetrated by a syringe;
    a substantially solid end cap on an end of said cage body wherein said end cap encloses said carrier receiving area; and
    wherein said port is located in said end cap.

5. An implantable device for locating within a body, said implantable device comprising:
    a body defining an outside surface;
    a carrier receiving area defined by said body;
    an un-doped collagen carrier material loaded in said carrier receiving area;
    a port that communicates said outside surface with said carrier receiving area for facilitating delivery of a biologically active substance onto said un-doped carrier material;
    a pathway that communicates with said carrier receiving area for delivering said biologically active substance from said carrier receiving area to a target bone structure;
    a plug in said port adapted to be penetrated by a syringe;
    a substantially solid end cap on an end of said cage body wherein
    said end cap encloses said carrier receiving area; and
    wherein said port is located in said end cap.

6. A bone implantable device for locating adjacent a target bone structure, said bone implantable device comprising:
    a body defining an outside surface;
    a carrier receiving area defined by said body;
    a pre-loaded collagen carrier material in said carrier receiving area, said pre-loaded collagen carrier material comprising a biologically active substance;
    a pathway that communicates with said carrier receiving area for delivering said biologically active substance from said carrier receiving area to the target bone structure;
    the interbody spine fusion cage further comprising:
        a substantially solid end cap on an end of said cage body wherein
        said end cap encloses said carrier receiving area; and
        wherein a port is located in said end cap;
        a plug in said port, said plug adapted to be penetrated by a syringe.

7. A bone implantable device for locating adjacent a target bone structure, said bone implantable device comprising:
    a body defining an outside surface;
    a carrier receiving area defined by said body;
    a pre-loaded sponge material in said carrier receiving area, said pre-loaded sponge material comprising a biologically active substance;
    a pathway that communicates with said carrier receiving area for delivering said biologically active substance from said carrier receiving area to the target bone structure;
    the interbody spine fusion cage further comprising:
        a substantially solid end cap on an end of said cage body wherein said end cap encloses said carrier receiving area; and
        wherein a port is located in said end cap;
        a plug in said port, said plug adapted to be penetrated by a syringe.

* * * * *